(12) United States Patent
Perryman et al.

(10) Patent No.: US 9,433,789 B2
(45) Date of Patent: Sep. 6, 2016

(54) METHOD, SYSTEM AND APPARATUS FOR REMOTE NEURAL MODULATION BRAIN STIMULATION AND FEEDBACK CONTROL

(71) Applicant: Micron Devices, LLC, Miami Beach, FL (US)

(72) Inventors: Laura Tyler Perryman, Scottsdale, AZ (US); Chad Andresen, Chandler, AZ (US)

(73) Assignee: Micron Devices LLC, Miami Beach, FL (US)

(*) Notice: Subject to any disclaimer, the term of this patent is extended or adjusted under 35 U.S.C. 154(b) by 0 days.

(21) Appl. No.: 14/214,432

(22) Filed: Mar. 14, 2014

(65) Prior Publication Data
US 2014/0277257 A1 Sep. 18, 2014

Related U.S. Application Data

(60) Provisional application No. 61/799,988, filed on Mar. 15, 2013.

(51) Int. Cl.
| A61N 1/36 | (2006.01) |
| A61N 1/05 | (2006.01) |
| A61N 1/372 | (2006.01) |
| A61B 5/00 | (2006.01) |
| A61B 5/0478 | (2006.01) |
| A61N 1/08 | (2006.01) |

(52) U.S. Cl.
CPC ........... *A61N 1/36125* (2013.01); *A61B 5/002* (2013.01); *A61B 5/0006* (2013.01); *A61B 5/0478* (2013.01); *A61B 5/4836* (2013.01); *A61N 1/0531* (2013.01); *A61N 1/0534* (2013.01); *A61N 1/36017* (2013.01); *A61N 1/37223* (2013.01); *A61N 1/36064* (2013.01); *A61N 1/36139* (2013.01); *A61N 2001/086* (2013.01)

(58) Field of Classification Search
CPC . A61B 5/0478; A61N 1/0531; A61N 1/0534
See application file for complete search history.

(56) References Cited

U.S. PATENT DOCUMENTS

| 8,892,208 B2 * | 11/2014 | Flynn | A61N 1/36 607/45 |
| 2010/0114281 A1 * | 5/2010 | Swoyer | A61N 1/0534 607/116 |
| 2012/0283800 A1 * | 11/2012 | Perryman et al. | 607/60 |

* cited by examiner

*Primary Examiner* — Joseph Dietrich
(74) *Attorney, Agent, or Firm* — Fish & Richardson P.C.

(57) ABSTRACT

A method, system and apparatus is presented for a wireless neural modulation feedback control system as it relates to an implantable medical device comprised of a radio frequency (RF) receiver circuit, one or more dipole or patch antenna(s), one or more electrode leads connected to at least one dipole or patch antenna(s), and at least one microelectronic neural modulation circuit, and an external or internally implanted RF device to neurally modulate brain tissue in order to treat medical conditions that can be mediated by neuronal activation or inhibition, such as Parkinson's, Alzheimer's, epilepsy, other motor or mood based disorders, and/or pain. The implantable receiver captures energy radiated by the RF transmitter unit and converts this energy to an electrical waveform by the implanted neural modulation circuit to deliver energy that can be utilized by the attached electrode pads in order to activate targeted neurons in the brain.

22 Claims, 23 Drawing Sheets

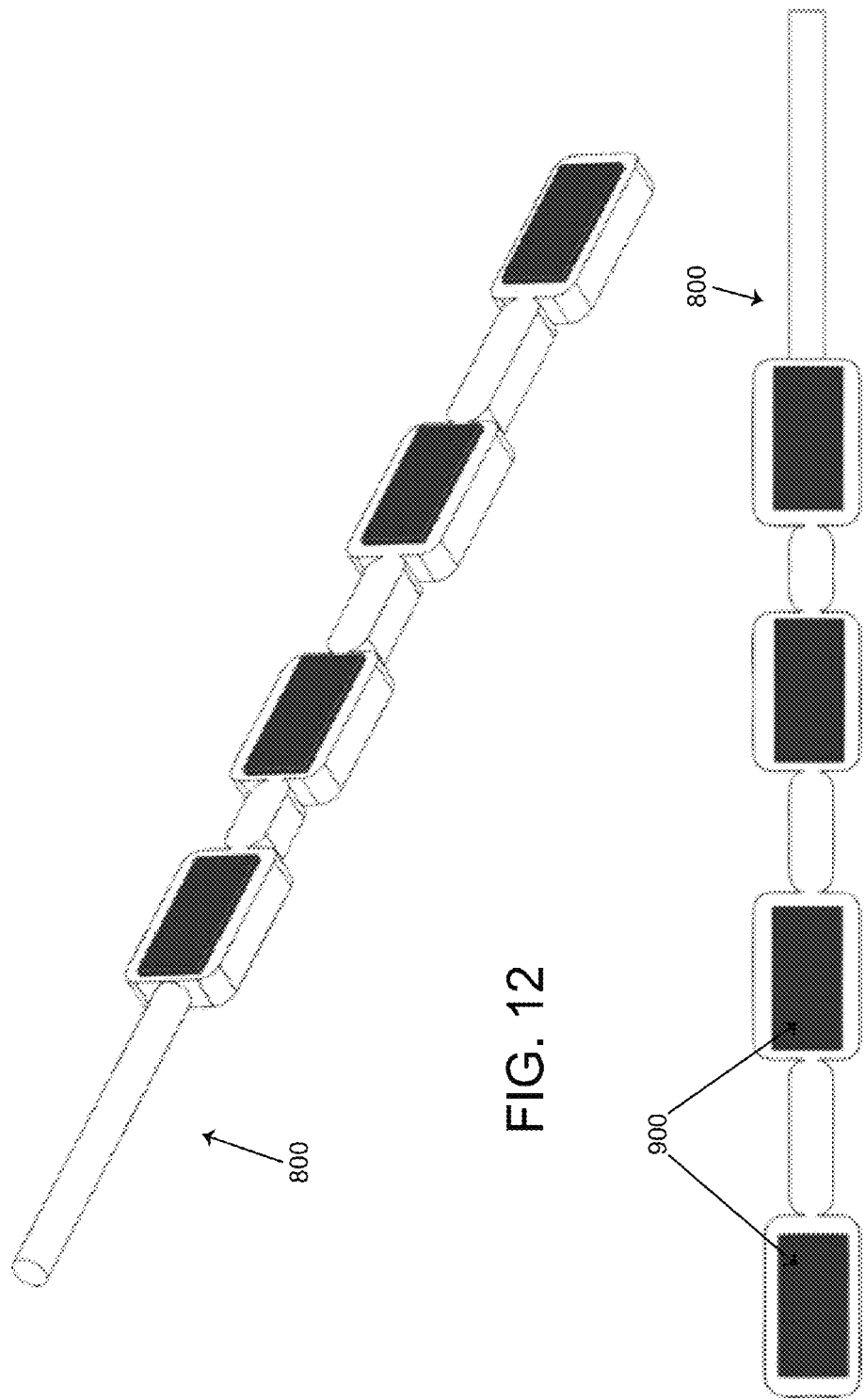

METHOD, SYSTEM AND APPARATUS FOR REMOTE NEURAL MODULATION BRAIN STIMULATION AND FEEDBACK CONTROL

CROSS-REFERENCE TO RELATED APPLICATION

This application claims the benefit of and priority to U.S. Provisional Patent Application Ser. No. 61/799,988, entitled "Method, System and Apparatus for Remote Neural Modulation Brain Stimulation and Feedback Control," filed Mar. 15, 2013.

BACKGROUND OF THE INVENTION

The present invention relates to systems and methods for providing stimulation to neurons of the brain and recording neuronic activity, and more particularly to systems and leads for wireless transmission of information to and from the stimulation/recording electrodes implanted at target areas of the brain.

Medically intractable epileptics often require combined video-EEG monitoring to determine candidacy for surgical treatment. Neurosurgeons frequently use intracranial depth electrode monitoring to determine seizure origination location. Current technology requires a wired connection to the implanted electrodes, which increases the risk of infection, is uncomfortable, and can only be used in the hospital setting. Current devices also only permit magnetic resonance imaging (MRI) at low field strengths, limiting resolution of clinical imaging. One way to improve these systems is to develop smaller, wirelessly powered leads.

Wireless leads can also be effective for recording neuronal activity, to provide a treatment option to provide home-based intracranial monitoring and stimulation in a closed-looped fashion for patients with severe brain anomalies and disorders. Current technologies for this type of monitoring require leads to be placed percutaneous through the skin, thereby increasing the chance of infection, are uncomfortable for the patient, and can only be used in the hospital setting.

SUMMARY

In one aspect of the present invention, a novel implantable lead is provided. The lead itself integrates both wireless recording and stimulation. The lead can be used for patients who require depth electrode implantation to localize the source of their seizures or other brain anomaly activity. In one embodiment, the invention comprises a 3T MRI compatible, wirelessly powered, 800 micron diameter lead to allow clinicians to record intracranial activity without percutaneous connections. In another embodiment, this lead can provide up to eight (8) electrode contacts for recording in a 20 cm long continuum with at least four (4) electrode contacts for stimulation current delivery and field steering. In still another embodiment, this small form factor lead can be placed near the hippocampus or entorhinal cortex with standard surgical techniques. In still another embodiment, this design also allows for placement of single neuron recording microwires through the lead lumen.

The present invention encompasses a wirelessly powered recording and stimulation device for deep brain applications to improve the treatment of neurological disorders. In one embodiment, the implantable wireless lead has special features for integration of the recorded data into $3^{rd}$ party EEG systems in real-time. In another embodiment, the system will allow for recording from up to eight (8) electrode contacts and stimulation from four (4) electrodes. In still another embodiment, the present invention comprises a closed loop system having the ability to optimize the clinical effect while minimizing the occurrence of side effects, namely a smaller, wirelessly powered lead integrating both recording and stimulation which can be used in patients who require depth electrode implantation to localize the source of their seizures or other brain anomaly activity and maintain 3T MRI compatibility.

In certain embodiments, by adapting the wireless recording and stimulation technology, the present invention is able to provide patients undergoing intracranial monitoring a method to localize the source of their seizures or other brain anomaly disorder with immediate benefits of greater mobility, increased comfort due to the lack of percutaneous open port connections, and decreased risk of infection. This technology can also provide the ability to perform intracranial monitoring in an outpatient setting, improving clinical utility by increasing the chances of capturing a patient's typical neuronal activity.

BRIEF DESCRIPTION OF THE DRAWINGS

FIG. 12 depicts a view of the wireless cortical stimulation/recording lead 800.

FIG. 13 depicts a view of the wireless cortical stimulation/recording lead 800 and its electrode configuration 900.

DETAILED DESCRIPTION

Figure 1:
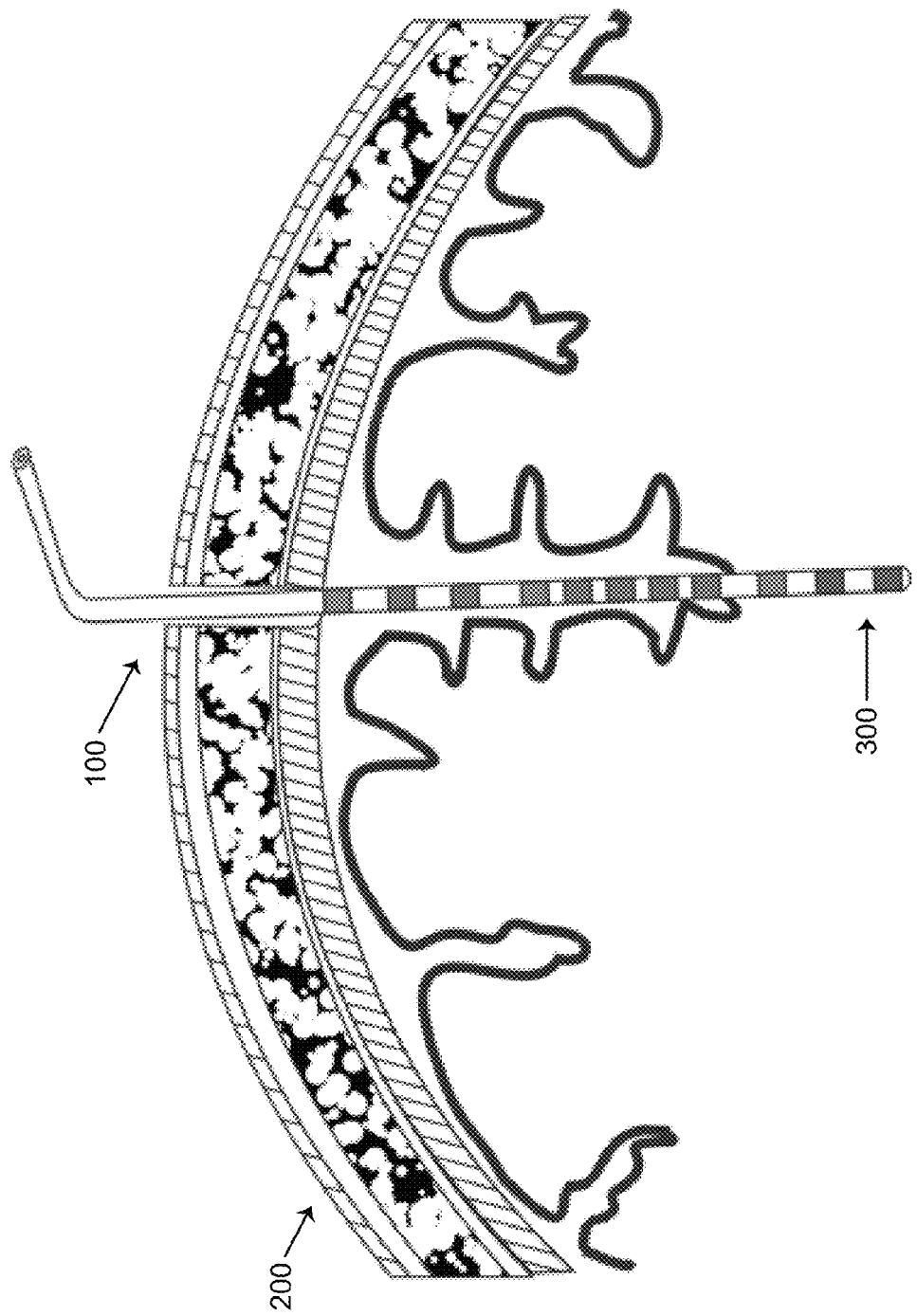
FIG. 1 depicts a wireless deep brain stimulation/recording lead 100 implanted near the subthalamic nucleus with portions of the lead 100 exiting through the cranial aspect of the cranium 200 during surgical implantation. Electrodes 300 are shown as shaded rectangles along the length of the body of the lead 100.
Figure 2:
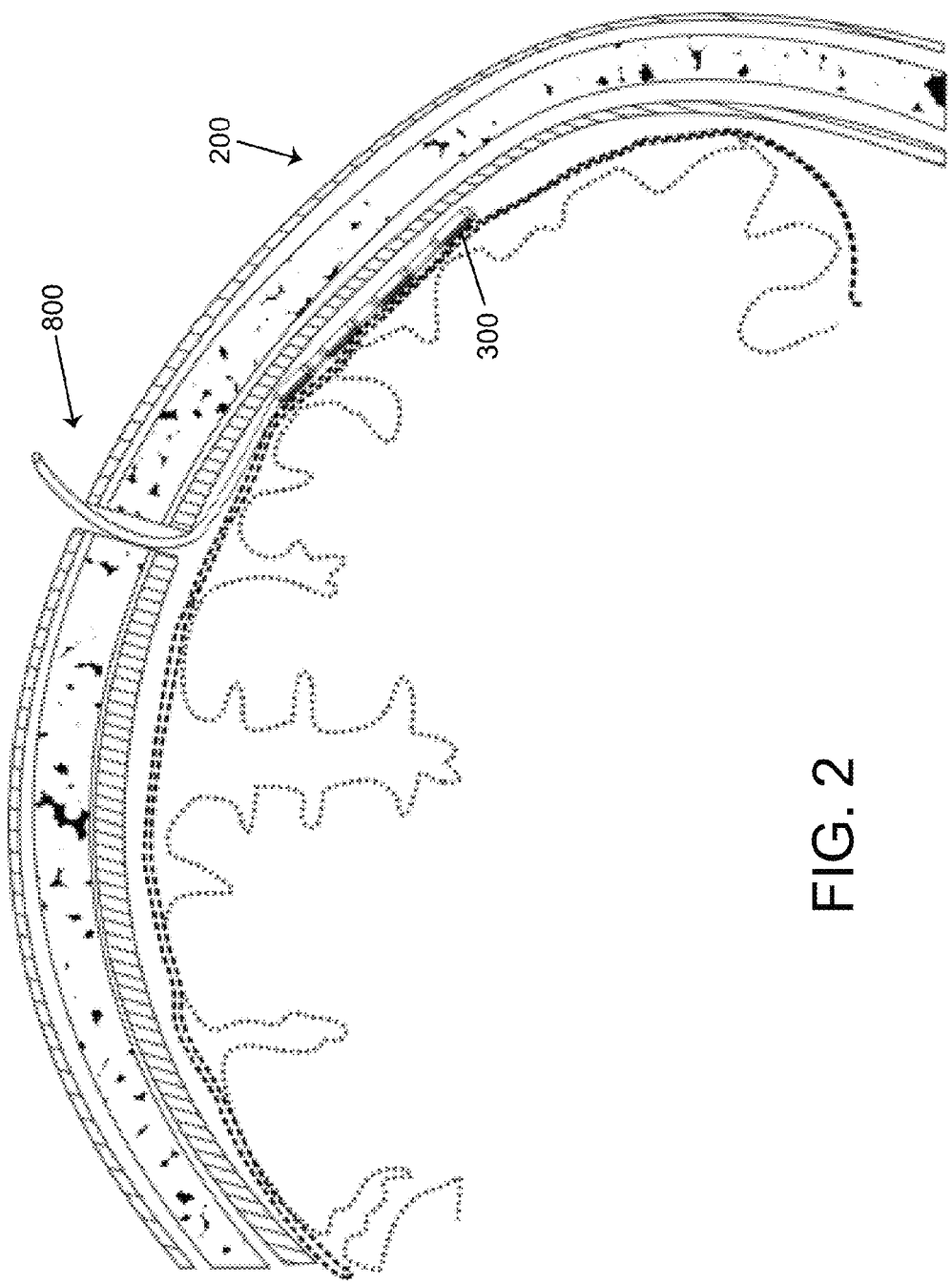
FIG. 2 depicts a wireless cortical stimulation/recording lead 800 implanted next to the cortical membrane with portions of the lead 100 exiting through the cranial aspect of the cranium 200 during surgical implantation.
Figure 3:
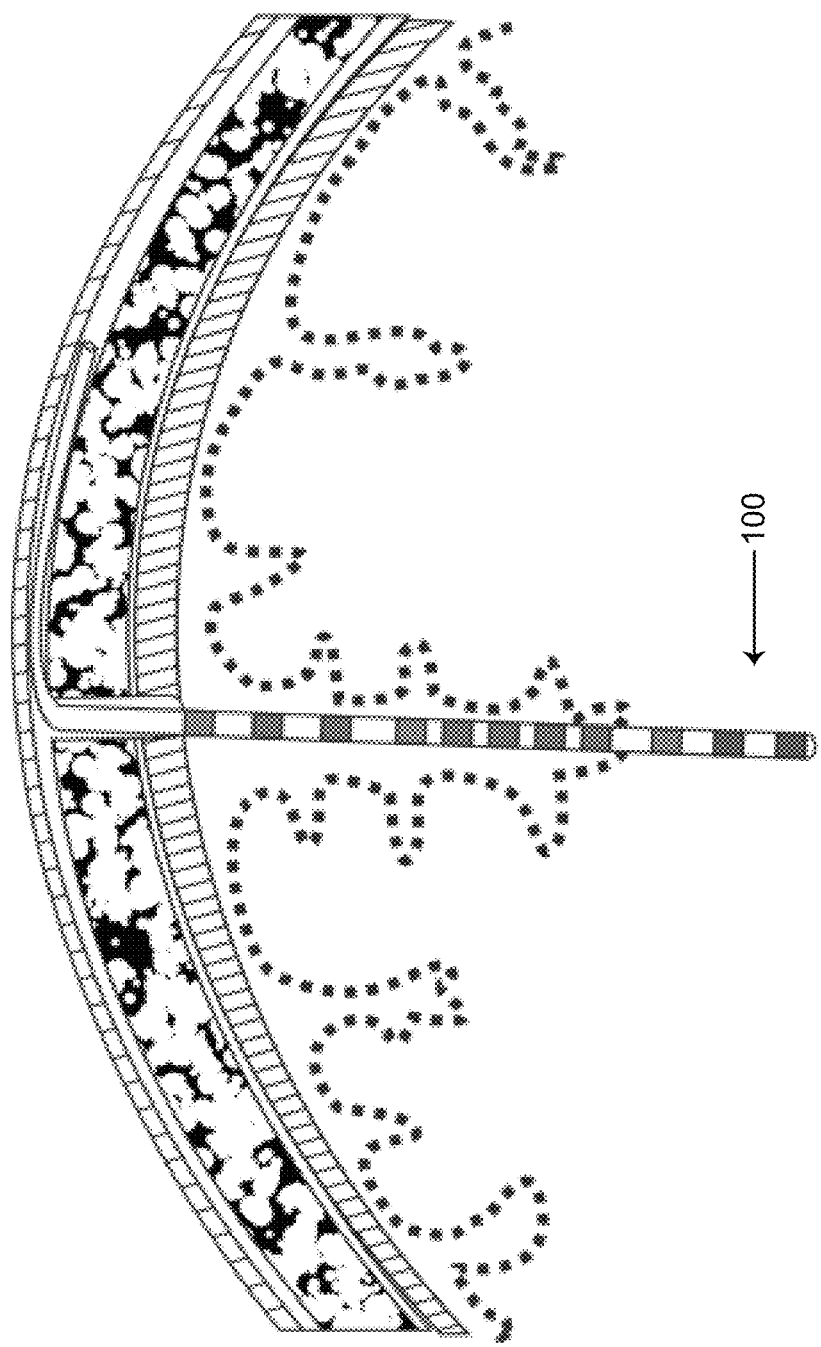
FIG. 3 depicts the lead 100 is fully implanted at a target deep brain region, such as at the subthalamic nucleus with the proximal tip anchored in position.
Figure 4:
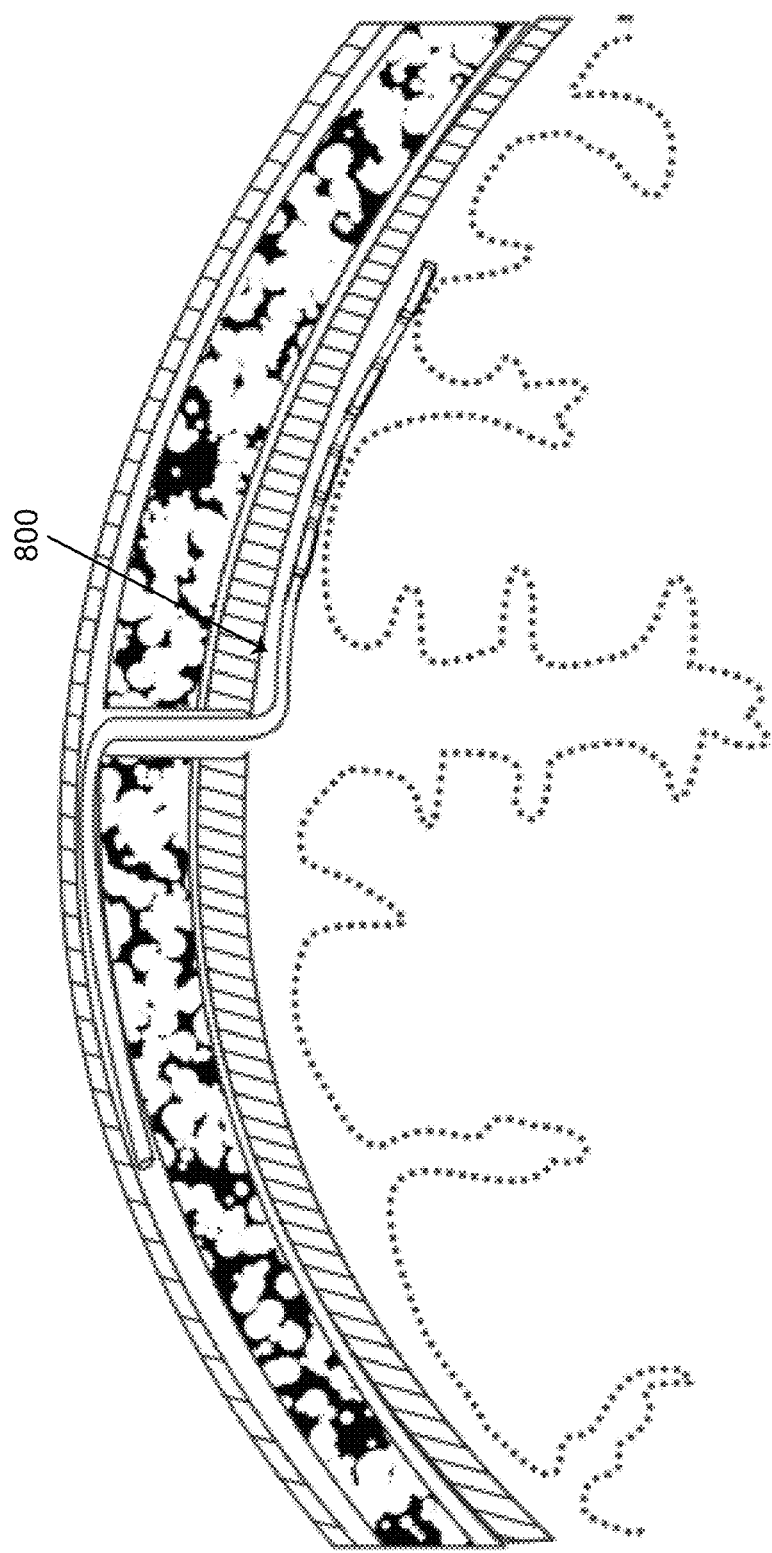
FIG. 4 depicts a fully implanted wireless cortical lead 800 and the termination of the proximal tip.
Figure 5:
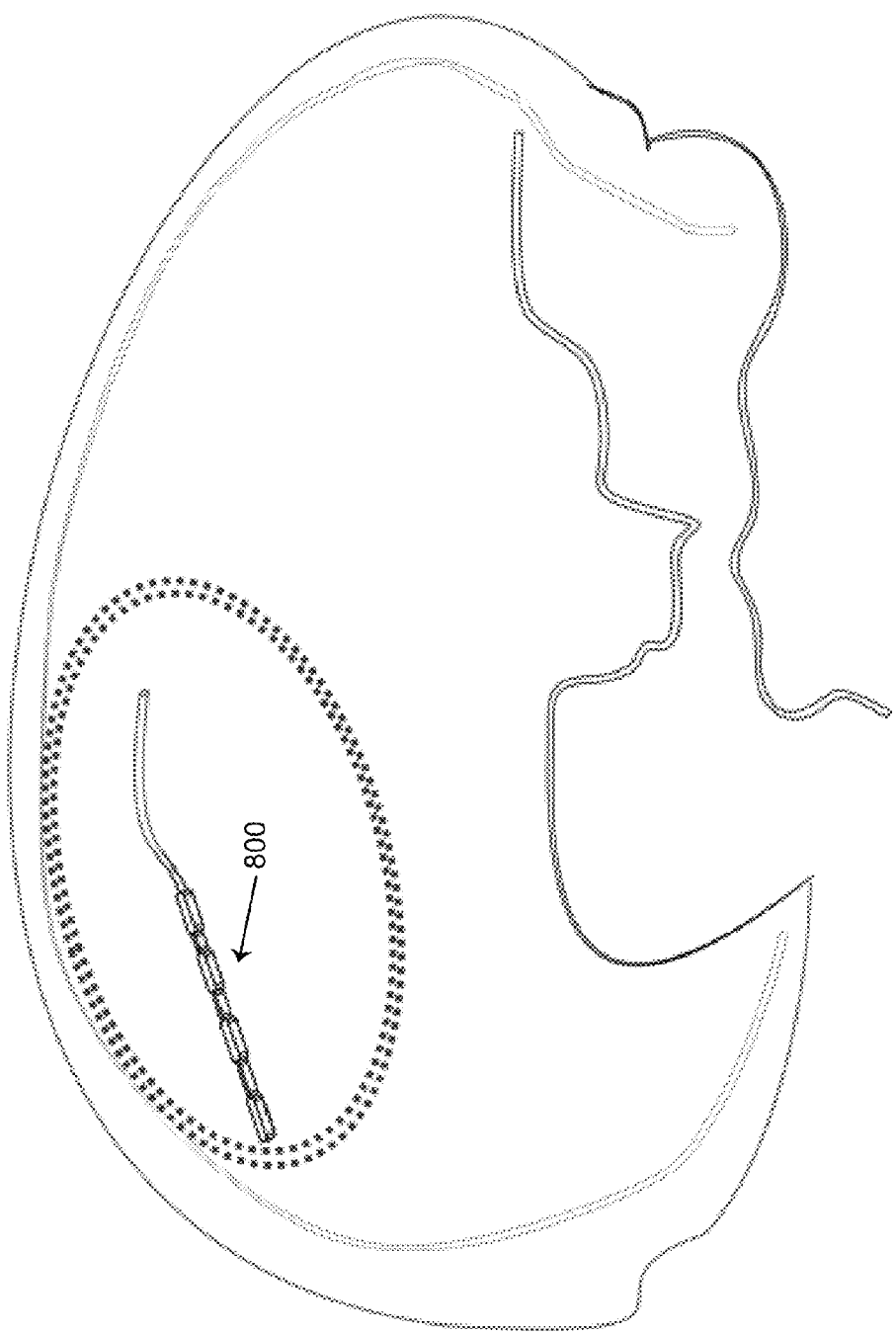
FIG. 5 depicts a fully implanted wireless cortical lead 800 and the termination of the proximal tip.

Referring to FIG. 1, shown is a deep brain stimulation/recording lead 100 according to an exemplary embodiment. In the figure, the lead 100 is shown during implantation of the lead near the subthalamic nucleus. In FIG. 3, the lead 100 is shown fully implanted at a target deep brain region, such as at the subthalamic nucleus with the proximal tip anchored in position. Similarly, referring to FIG. 2, shown is a cortical stimulation/recording lead 800 according to an exemplary embodiment during implantation of the lead next to the cortical membrane. In FIGS. 4-5, the lead 800 is shown fully implanted at a target cortical region of the brain, with the proximal tip anchored in position. As shown, exemplary leads 100 and 800 include one or more electrodes 300 which may be used for stimulation and/or recording when implanted.

Various embodiments of lead 100 and 800, such as those shown implanted in the brain in FIGS. 1-5 may be used to create a full-scale, closed-loop system for recording neuronal activity that enables a patient to have home-based evaluations rather than in-patient stays. Additionally, leads 100, 800 according to the exemplary embodiments would eliminate tunneling to an implanted pulse generator (IPG) through the neck where there is the potential for kinking the extension wires, and a source of infection and discomfort in some patients.

In exemplary embodiments of the present invention, one or more of the following features are present: (i) use of a wireless lead for neuronal monitoring, eliminating the need for percutaneous connections; (ii) development of a non-tethered data recording system, thereby improving patient mobility; (iii) analysis of stimulation-related effectiveness with simultaneous recording; and (iv) integration of a wireless lead with existing EEG-video telemetry systems, thereby optimizing use of existing capital investments.

Figure 6:
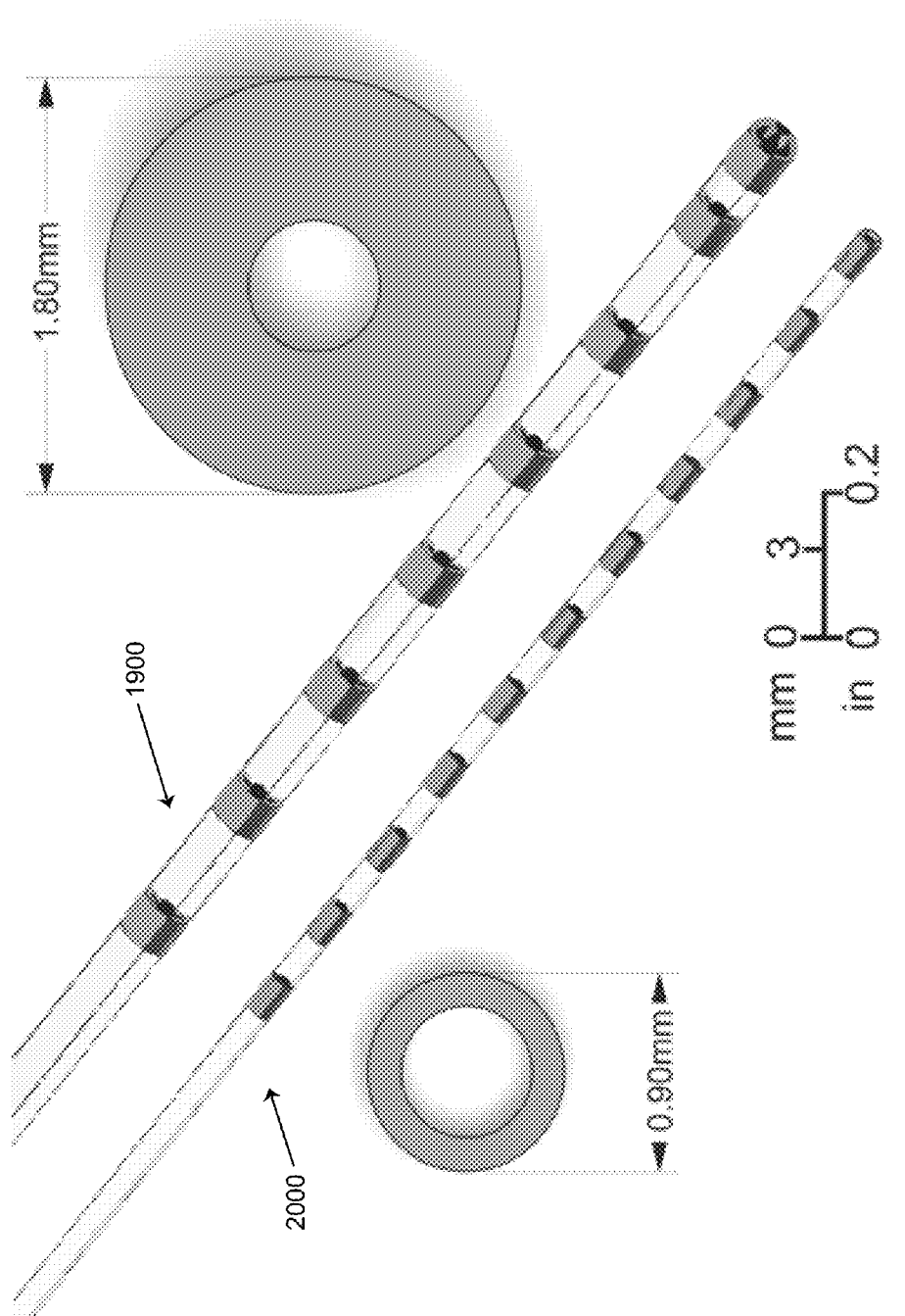
FIG. 6 depicts one embodiment of a wireless lead having an 800 micron diameter, that is approximately over 50% smaller than existing wired leads.
Figure 7:
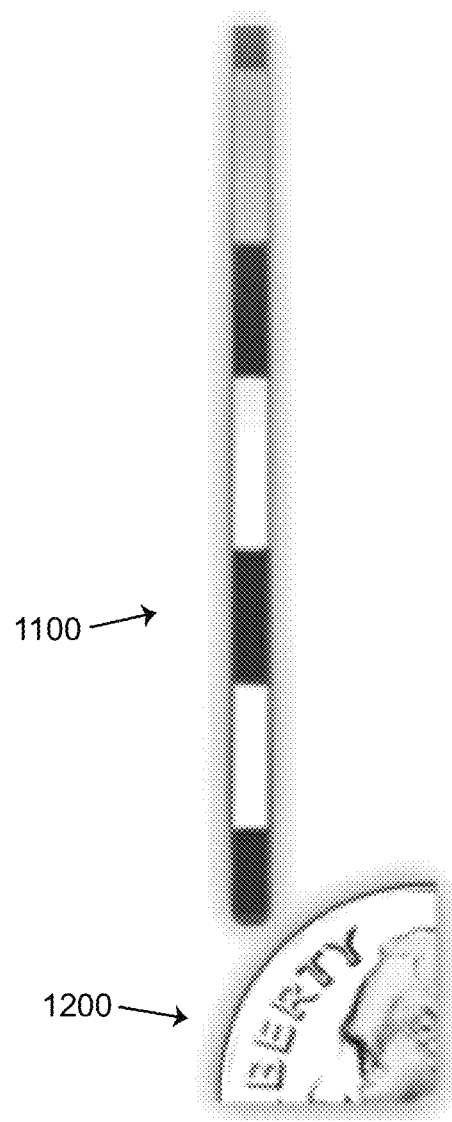
FIG. 7 depicts the size of a wireless deep brain stimulation/recording lead 1100 in comparison to currency 1200.
Figure 8:
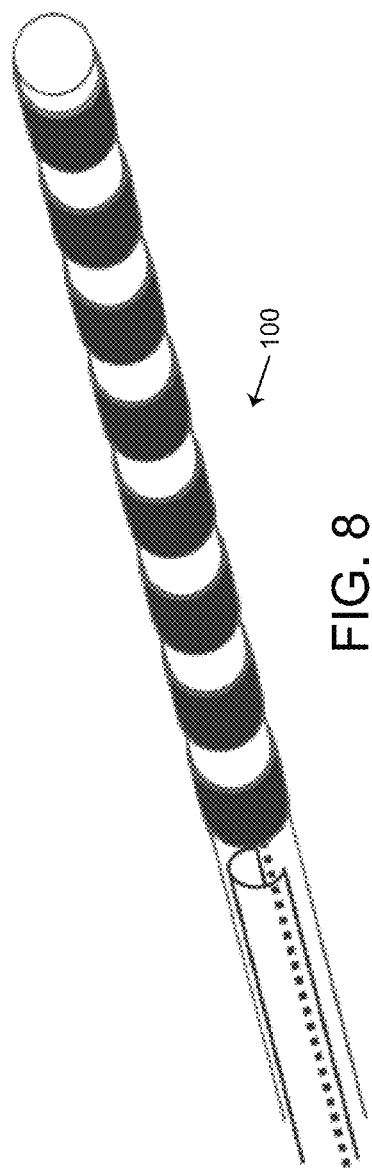
FIG. 8 depicts a view of the wireless deep brain stimulation/recording lead 100.

In one aspect of the present invention, a micro-assembly process for a clinical grade wirelessly powered intracranial recording and stimulation lead for neuronal monitoring and therapy has been developed. In one embodiment, a wireless lead 100 has an 800 micron diameter, that is approximately over 50% smaller than existing wired leads, as depicted in FIG. 6. FIG. 7 also depicts the small size of a lead 1100 according to an exemplary embodiment, shown relative to a piece of currency 1200 for illustrative purposes. FIGS. 8-11 depict exemplary embodiments of the deep brain stimulation/recording lead 100. As shown, particularly in FIG. 9, electrodes 300 may take on various configurations on the body of the lead 100. As shown in FIG. 10, the deep brain stimulation/recording lead 100 contains an electronics package 600 to power the lead for stimulation or recording.

Figure 9:
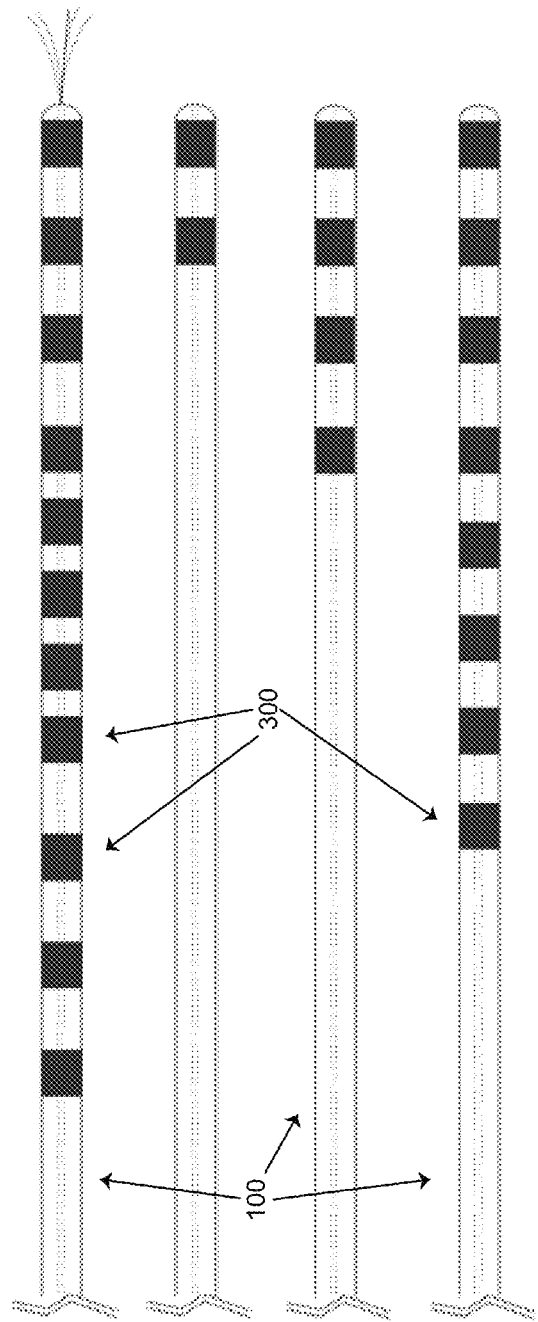
FIG. 9 depicts a view of the wireless deep brain stimulation/recording lead 100 and its various electrode 300 configurations.
Figure 10:
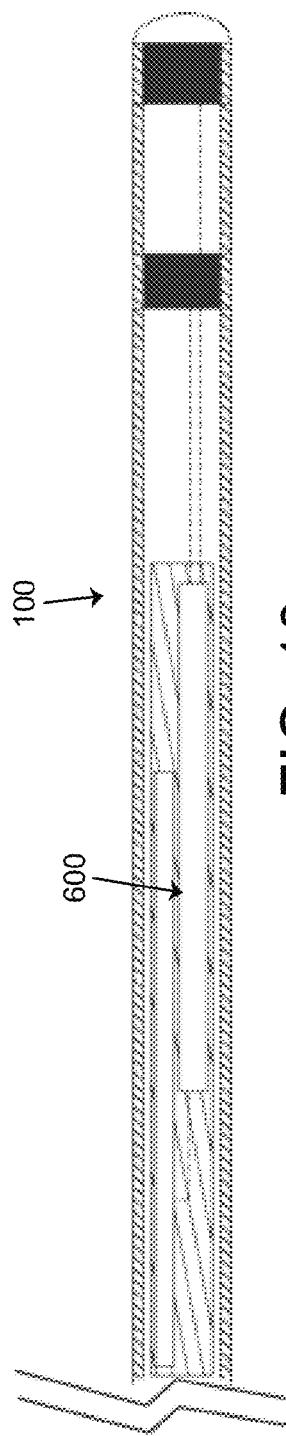
FIG. 10 depicts a cutout view of the wireless deep brain stimulation/recording lead 100 and the electronics 600 that power it.
Figure 11:
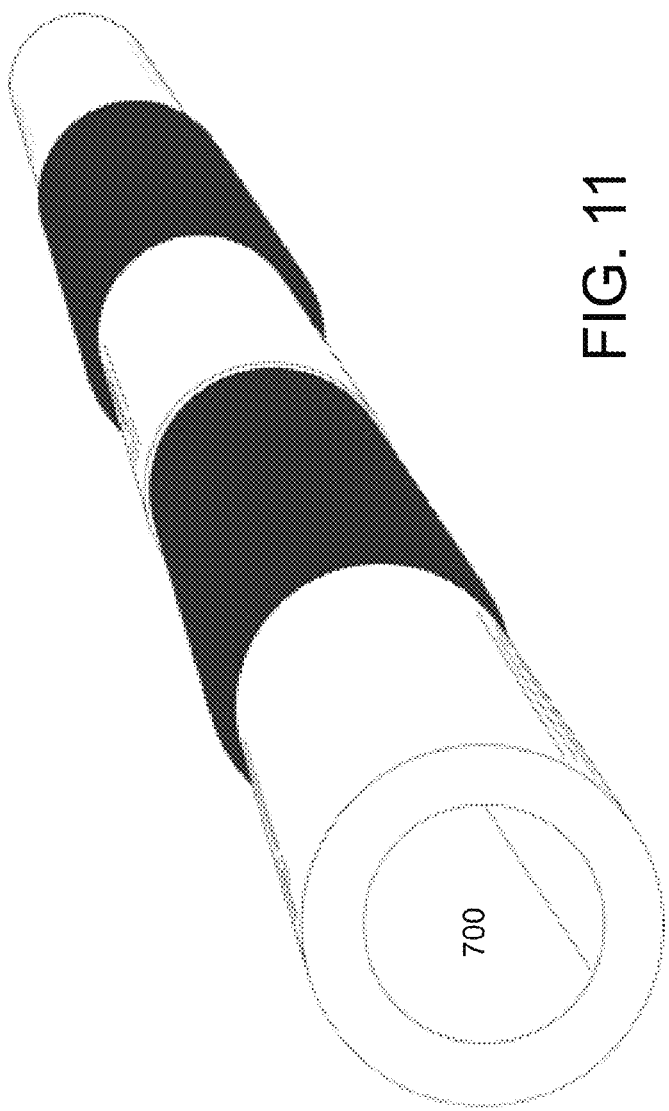
FIG. 11 depicts a profile view of the wireless deep brain stimulation/recording lead's large inner channel 700 used to give access to steering devices or micro recording wires.
Figure 15:
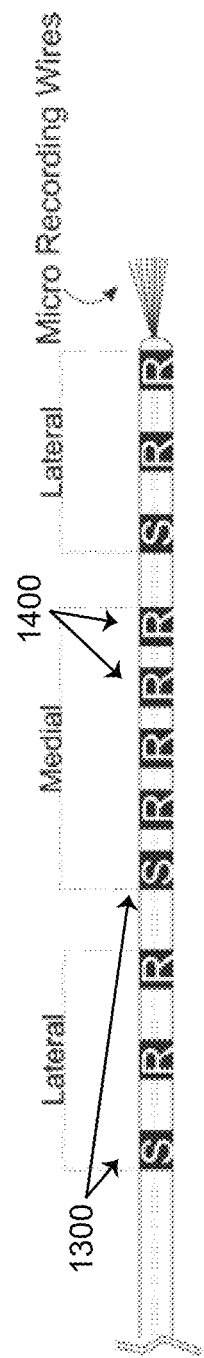
FIG. 15 illustrates a wireless deep brain stimulation/recording lead and electrode assignments for stimulation (S) 1300 and recording (R) 1400.

In some embodiments, microwires can be inserted through the lead 100 while the stimulation electrodes are also enabled, as depicted in an embodiment in FIG. 9 and in FIG. 15. This will provide researchers with additional datasets not previously available for a variety of future investigations. As shown particularly in FIG. 11, the wireless lead 100 may include a channel 700 which may allow for the insertion of the microwires. In preferred embodiments, the lead 100 may include a multi-lumen channel which allows for the insertion of up to nine, 38 micron diameter single axon recording wires into lead.

Figure 14:
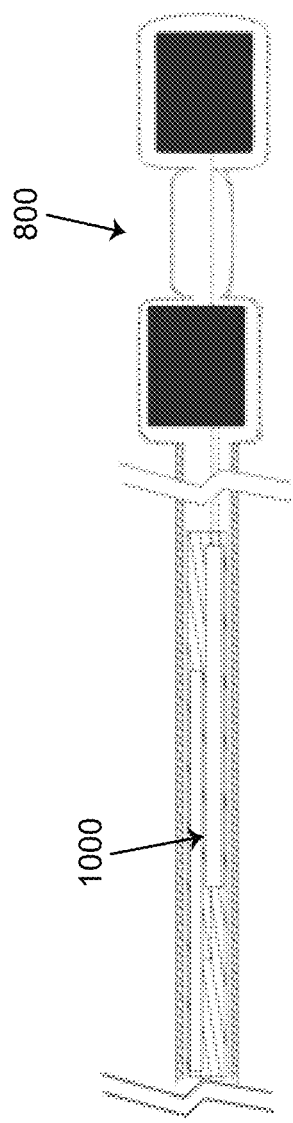
FIG. 14 depicts a cutout view of the wireless cortical stimulation/recording lead 800 and the electronics 1000 that power it.

FIGS. 12-14 depict exemplary embodiments of a cortical stimulation/recording lead 800. In the embodiments shown, cortical stimulation/recording lead 800 comprises one or more electrodes 900 spaced along the length of lead 800. The electrodes may be uniformly spaced, or may spaced at varying distances along the lead 800. As shown, the electrode portions may be separated by intermediate portions having a smaller width or diameter than the electrode portions.

In exemplary embodiments, lead 100, 800 can provide up to eight (8) electrode contacts 300 for recording with at least four (4) electrode contacts for stimulation current delivery and field steering. In preferred embodiments, the electrode contacts are located in a 20 cm long continuum. The leads are also preferably 3T MRI compatible. As shown in FIG. 15, the stimulation electrodes 1300 and the recording electrodes 1400 can be arranged intermixed along the length of the lead body. Various configurations and arrangements of stimulation and recording electrodes may be used, and may depend on the area of stimulation/recording, type of stimulation being provided, or the activity intended to be recorded.

Figure 16:
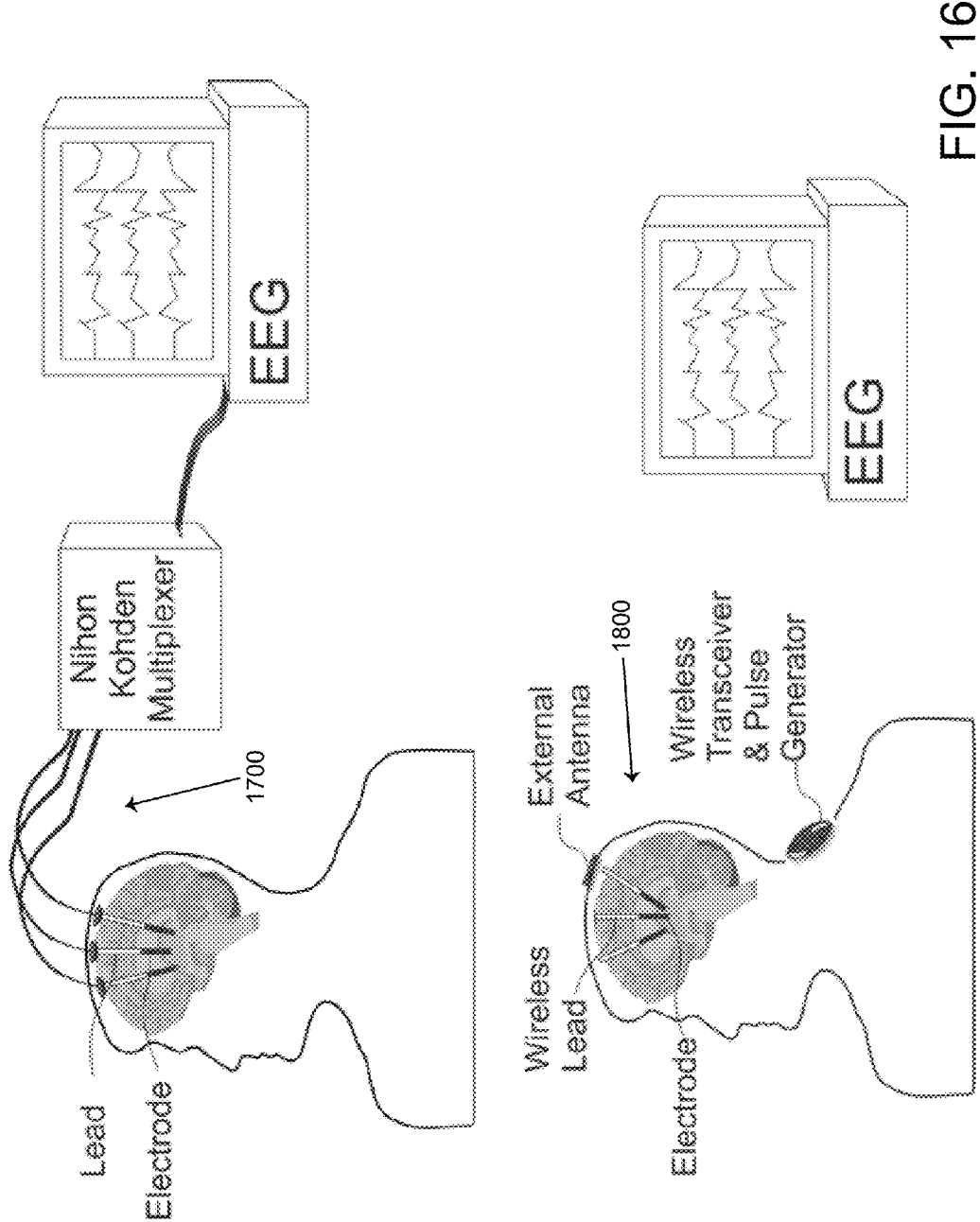
FIG. 16 illustrates a comparison between a wired stimulation/recording system 1700 to a wireless recording system 1800 and their components.
Figure 17:
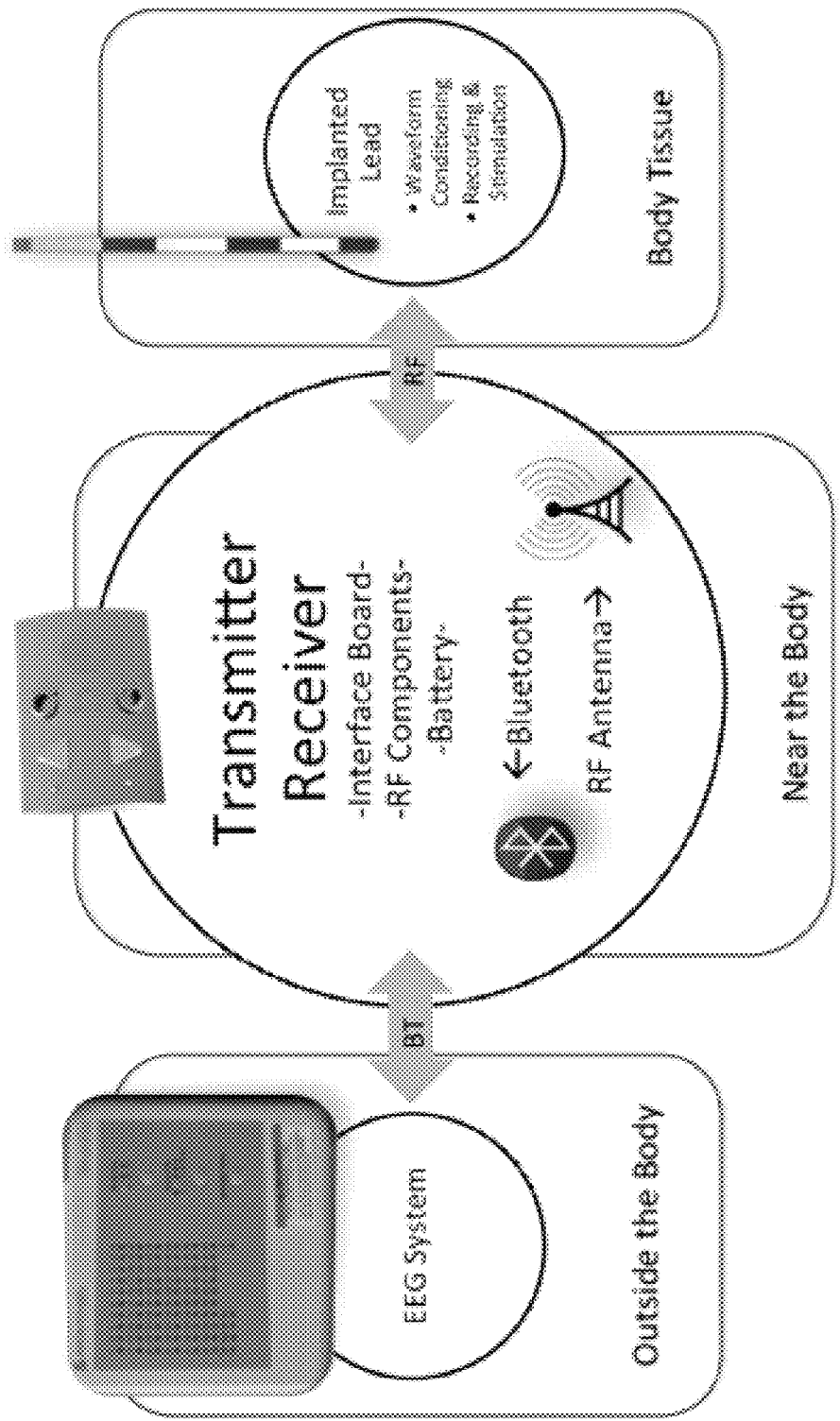
FIG. 17 illustrates the component interactions for a wireless stimulation/recording system.

As depicted in FIGS. 16 and 17, a wireless stimulating/recording system 1800 according to an exemplary embodiment includes a wearable data collection device and interface to send recorded data to a standard EEG telemetry system. This on-body device has the capability of collecting both the single axon micro-wire recording electrode data and the action potential data from the at least one electrode 300. In a preferred embodiment, data is collected from eight (8) recording electrodes at 30 kHz. In other embodiments, a 16 bit analog recording data is transmitted from the wireless implant device and converted into a digital format to be sent via Bluetooth to an EEG system for interpretation and detection of localized neuronal activity. In some embodiments, the EEG system is a $3^{rd}$ party EEG system.

The present invention encompasses a system that includes a controller-transmitter, an implanted device (shown implanted in the brain in FIG. 16), a programmer to adjust parameters, and electrode pads that are in contact or in proximity with neurons in the brain in order to facilitate the treatment through volume conduction. In another aspect of the invention, the system incorporates concepts that have an advantage over other devices, including introducing features that eliminate the requirement for implantable wired electrical leads and implantable pulse generators as shown in the wired system 1700 of FIG. 16. In a further aspect of the invention, the apparatus can utilize a controller-transmitter unit that is external to the body. The controller-transmitter unit can be incorporated into a belt or harness design in close enough proximity to allow for electrical radiated coupling through the skin and underlying tissue in order to actuate the implanted device.

In certain embodiments of the invention, the transmitter is remotely programmed by Bluetooth® (Bluetooth is the copyright of the Bluetooth Special Interest Group) to the patient control unit or clinician's programmer unit. The parameters that can be controlled include one or more of the following: pulse amplitude, pulse frequency, and pulse width in the ranges shown in Table 1. The patient and/or the clinician can also optionally control duration and pattern of treatment.

| Stimulation Parameter Table 1 | |
|---|---|
| Pulse Amplitude: | 0 to 10 mA |
| Pulse Frequency: | 0 to 20000 Hz |
| Pulse Width: | 0 to 1 ms |

In still other embodiments, the controller-transmitter is utilized by the patient and/or the clinician to program the parameter settings. For example, the clinician may have the option of locking out the patient's ability to adjust certain parameters, or leaving the option for all parameter adjustments.

This invention also relates to a feedback control system method for an RF near field powered implantable apparatus which will selectively produce electrical stimulus signals and a lead adapted to carry the stimulus signals to the targeted neurons in the brain. In certain embodiments, each implanted device is configured to be monitored and/or controlled by an external or a subcutaneously implanted remotely placed controller in the receiver unit that is communicated with via a wireless communication channel. In another embodiment of the invention, the system may consist of a transmitter that sends parameter setting commands in regards to amplitude, pulse width and frequency to implanted devices via RF wireless energy and a receiving unit that receives signals back from at least some of said implanted devices. The option for a closed loop is included herein. In other embodiments, the transmission and the receiving can be operated in open loop fashion.

In other embodiments, the signal is transmitted to a receiver located in the transmitter unit to indicate the strength of the stimulus provided to the neurons by means of coupling the signal to the implanted dipole antenna, which radiates the telemetry signal to the external (or remotely implanted) receiver. The signal may consist of either or both an analog and digital telemetry pulse modulated carrier signal. The digitized data can be stored in an internal memory device within the implanted stimulator. The frequency of the carrier signal is preferably in the range of at least 300 megahertz to 8 gigahertz and the telemetry signal output bit rate is preferably at least 8 kilobits per second.

Figure 18:
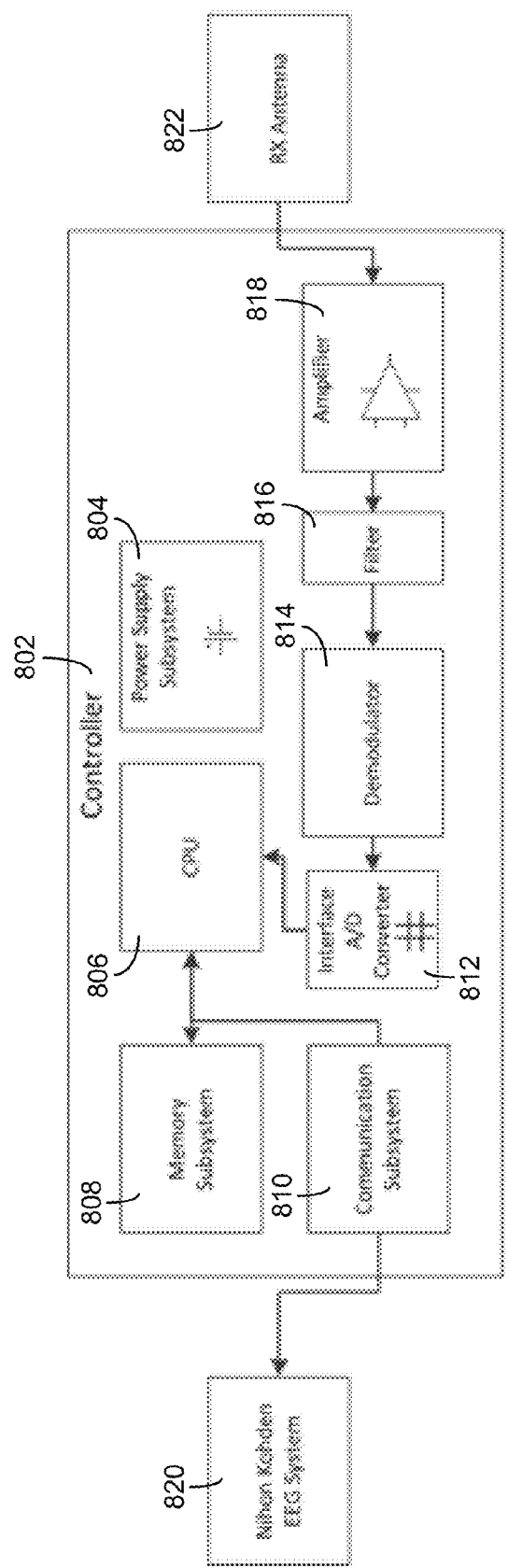
FIG. 18 illustrates the wireless transceiver sub-system responsible for recording the brain activity and sending telemetry to the control unit.

FIG. 18 illustrates the wireless transceiver sub-system responsible for recording the brain activity and sending telemetry to the control unit. The receiver may include an antenna 822 which receives the telemetry signal. The antenna 822 may pass the telemetry signal to an amplifier 818 of the controller of the receiver. The amplifier 818 may amplify the received telemetry signal. The amplifier 818 may be in communication with a filter 816 which filers the amplified telemetry signal. The filter 816 may be in communication with a demodulator 814. The demodulator 814 may demodulate the filtered telemetry signal. The demodulated signal may be converted from an analog signal to a digital signal (e.g., digitized) by an analog to digital converter 812 (e.g., interface A/D converter). The digitized signal may be passed to a microprocessor 806 (e.g., CPU). The microprocessor 806 may store the signal in memory 808 (e.g., memory subsystem). Memory 808 may be used to store instructions, programs, code, or other data which the microprocessor 806 uses to perform the functions described herein. For example, the memory 808 may contain a look up table used in estimating the current and/or shape of energy across an implant. Memory 808 may also contain an algorithm used to adjust the power output of a transmitter in response to the comparison using the look up table. A communication subsystem 810 may be used to communicate with an EEG system 820 (e.g., for acting on the information or instructions received in the telemetry signal). As shown in FIG. 18, Nihon Kohden EEG system 820 may receive information from the communication subsystem 810. Although a Nihon Kohden EEG system is illustrated, other EEG systems (e.g., control systems) may be used with the receiver/controller. The communication subsystem 810 may include a transmitter used to transmit energy to an implant (e.g., via RF, via induction, via a lead, etc.). In other embodiments, the receiver/controller includes a transmission antenna used to transmit energy to an implant. In further embodiments, the antenna illustrated as a receiving antenna may also be used for transmission of RF energy to an implant. A power supply subsystem 804 may provide electrical power to one or more of the components described herein.

Figure 19:
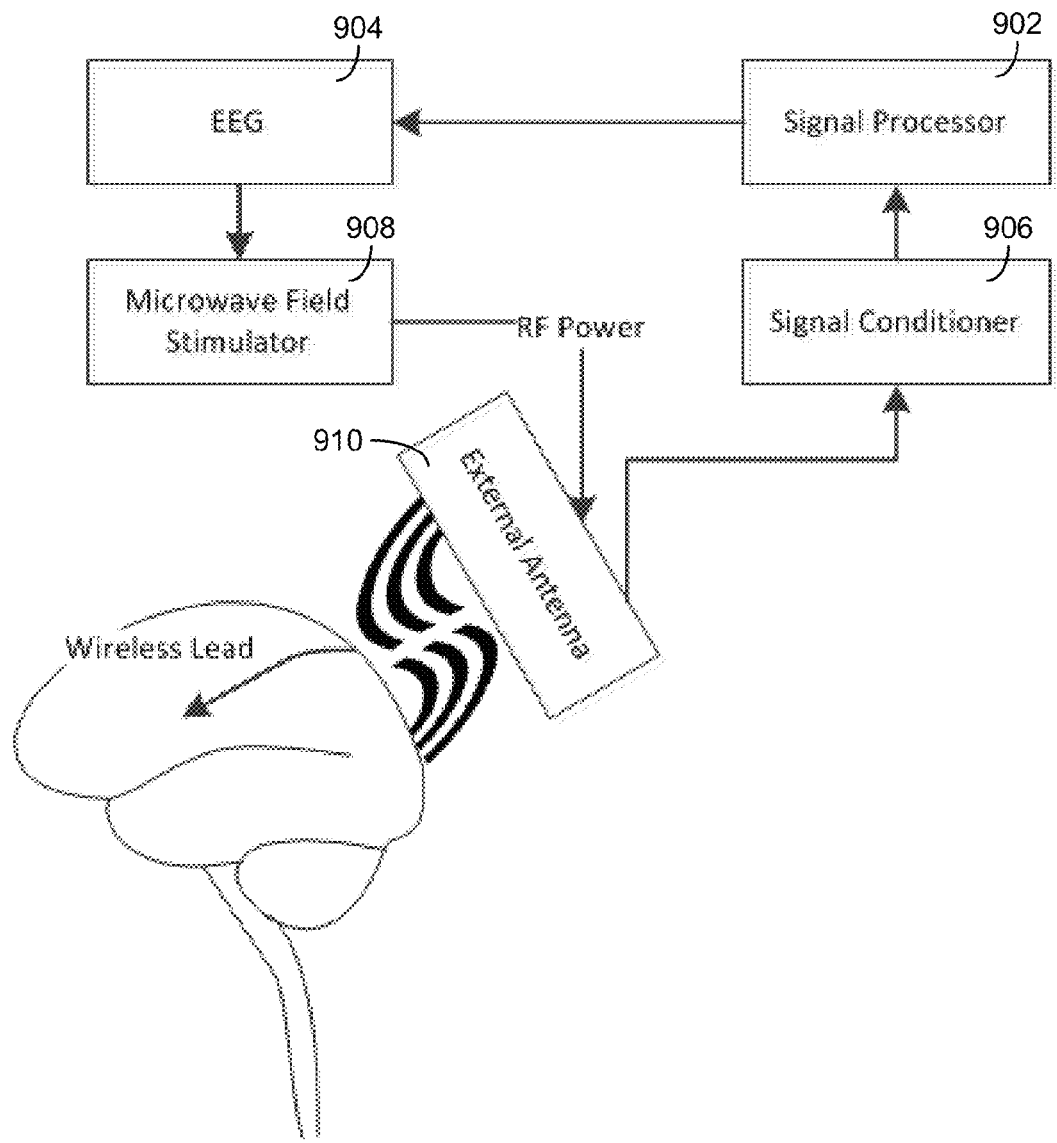
FIG. 19 depicts a block diagram of system components in communication.

FIG. 19 depicts a block diagram of system components in communication. A wireless lead may generate a telemetry signal which may be received by an external antenna 910. The external antenna 910 may pass the signal to a signal conditioner 906. The external antenna 910 may be included in a receiver/controller. The signal conditioner 906 may filter, amplify, demodulate, convert, or otherwise condition the telemetry signal. The functions of the signal conditioner 906 may be performed by one or more of an amplifier, filter, demodulator, and A/D converter of a receiver/controller. The conditioned telemetry signal may be passed to a signal processor 902. The signal processor 902 may analyze the signal. For example, the signal processor 902 may compare the information of the telemetry signal to a look up table estimating the current and/or shape of the energy across an implant. The functions of the signal processor 902 may be performed by a microprocessor (e.g., CPU) and/or memory of a receiver/controller. Information from the telemetry signal may be passed to an EEG module or machine 904 (e.g., using a communication subsystem of a receiver/controller). The EEG module or machine 904 and/or a receiver/controller may provide signal parameters or characteristics to a microwave field stimulator 908. The microwave field stimulator 908 may create RF power which may be transmitted to the wireless lead using an external antenna 910. In some embodiments, the microwave field simulator 908 and/or external antenna 910 are components of a receiver/controller.

Figure 20:
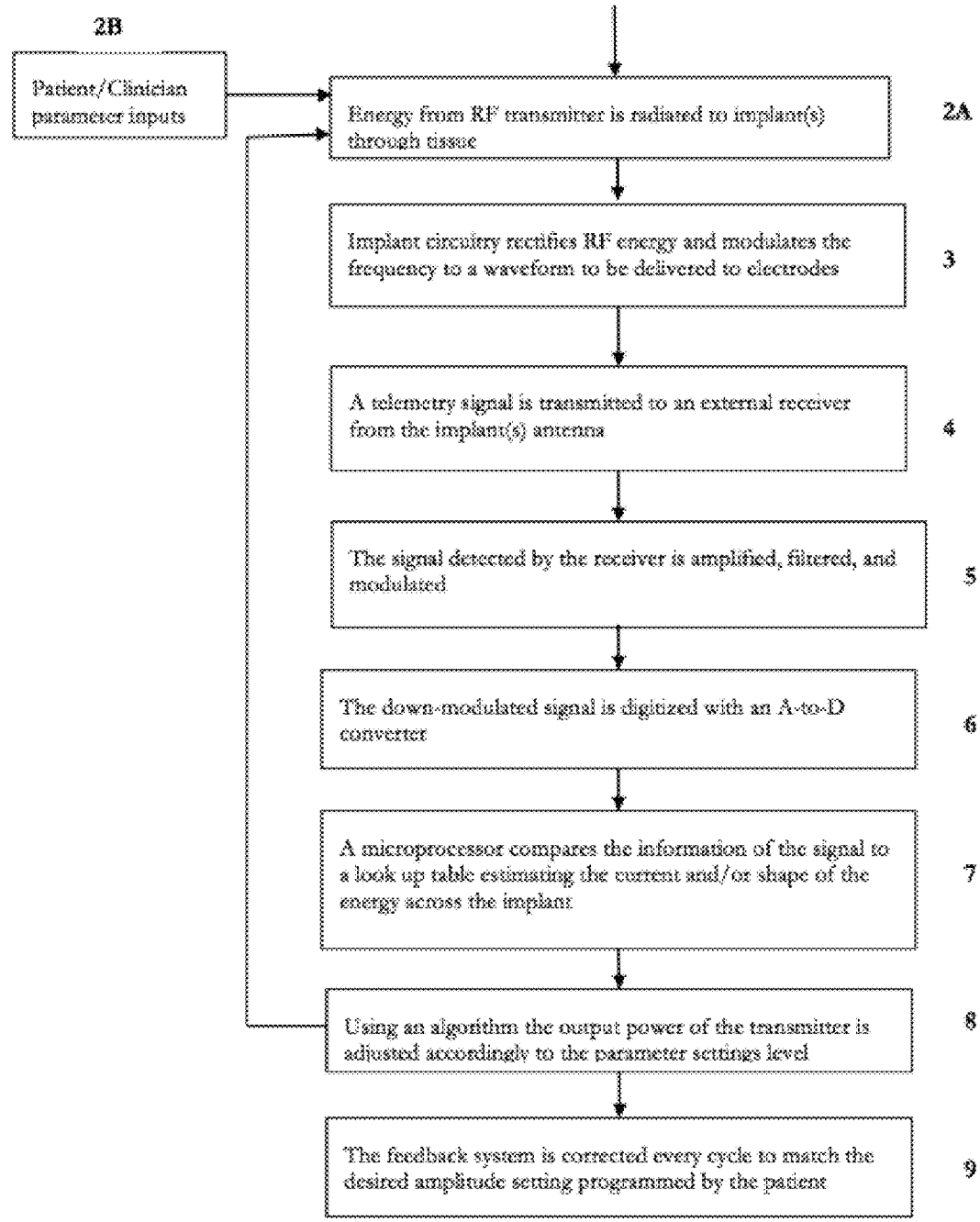
FIG. 20 depicts the decision tree used for powering, monitoring and adjusting stimulation parameters for the system.

Implantable wireless devices are initially programmed to meet the specific particular parameter settings for each individual patient during the initial implantation of the device. Because medical conditions or the body itself can evolve over time, the ability to re-adjust the parameter settings is required in order to not degrade the effectiveness of the therapeutic functionality. In another embodiment, the programming of the controller of the present invention is done with an external programming unit that sets the frequency, pulse width, and amplitude that will be transmitted by radiofrequency link to the wireless implanted dipole antenna. FIG. 20 depicts a decision tree for powering, monitoring, and/or adjusting stimulation parameters for the system.

With reference to FIG. 20, patient/clinician parameter inputs may be provided to the external programming unit (2B). These inputs may be parameters used by or affect the wireless implanted device. For example, the inputs may include or set the frequency, pulse width, and amplitude that will be transmitted by radiofrequency link to the wireless implanted dipole antenna. Based in whole or in part on the parameter inputs, energy from the radio frequency transmitter may be transmitted (e.g., radiated) to one or more implanted wireless devices (2A). The energy (e.g., radio frequency electromagnetic radiation) may travel through tissue and be received by the implant(s). Implant circuit may receive the RF energy and rectify the received transmission (3). This may include modulating received energy to create a waveform to be delivered to electrodes included in the implanted device. In some embodiments, the implant circuitry modulates the received RF frequency to create the waveform for delivery to the electrodes based on patient/clinician parameter inputs. These inputs may be received by the implanted device through a radiofrequency link to an external programming unit.

The implanted device may provide a telemetry signal to an external receiver (4). The telemetry signal may be based on measurements of the implanted device. In some embodiments, the implanted device includes a transmitter used to transmit the telemetry signal to the receiver. The receiver may detect the telemetry signal transmitted by the implanted device. The external receiver may process the signal received from the implanted device (5). For example, the external receiver amplify, filter, modulate, and/or otherwise process the telemetry signal. In some embodiments, the external receiver down-modulates the signal. The external receiver may then digitize the down-modulated signal using an analog to digital converter (6). A microprocessor may then compare the digitized telemetry signal to a look up table and estimate the current and/or shape of the energy across the implant (7). The microprocessor may be included in the external receiver. The microprocessor may then use an algorithm to adjust the power output of the RF transmitter (8). For example, the algorithm may use the estimated current and/or shape of the energy across the implant to determine one or more parameter setting levels (e.g., power, frequency, modulation, etc.). The parameter setting levels may be used by the RF transmitter to change the characteristics of the RF energy radiated to the implant through the tissue. For example, the RF transmitter may radiate energy to the implant with the characteristics of the energy and/or transmission based on the parameter setting levels determined by the algorithm. These steps may be performed in an iterative manner with the RF transmitter radiating energy to the implant, the implant sending a telemetry signal to the receiver and the receiver adjusting the characteristics of the energy radiated to the implant based on the telemetry signal (e.g., by processing the telemetry signal using one or more algorithms). The feedback system, as described, is corrected every cycle to match the desired amplitude setting programmed by the patient/clinician (9). In other words, the receiver and/or microprocessor use the telemetry signal from the implant in order to determine the amplitude and adjust the parameters used by the transmitter to radiate energy to the implant in order to match the actual amplitude (e.g., as measured by the implant and communicated with the telemetry signal) to the setting programmed by the patient/clinician. Aspects and/or components used in this process are discussed in greater detail as follows.

In still other embodiments, a telemetry signal will be transmitted by the modulation of the carrier signal outwardly to the receiver unit (through the skin if external, or through other body tissues if the receiver is implanted under the skin) The telemetry signal may be used to modulate the carrier signal (microwave frequency) that is coupled onto the implanted dipole antenna and does not interfere with the input to the dipole antenna that is received on the same lead to power the implant.

The telemetry signal may be coupled to the modulated signal on the dipole antenna, during the on and off state of the transistor circuit to enable or disable a waveform that produces the corresponding bursts necessary to transmit to the external (or remotely implanted) receiver. The end of the dipole antenna may act as an anode to provide a return path for the transmitted signal. In still other embodiments, diodes are connected in parallel to prevent excessive voltage from being coupled back to the oscillator. In yet another embodiment, a capacitor A/D converter can be used to transfer the stored data to a serialized pattern that can be transmitted on the pulse modulated signal from the internal dipole antenna neural stimulator.

In an exemplary embodiment, an apparatus for wireless neural modulation brain stimulation includes one or more implantable electrode leads, such as leads 100 or 800, for placing in proximity to neurons to be stimulated. The leads include at least one electrode 300 for providing stimulation and at least one separate electrode for collecting data. The apparatus further includes a first receiver configured to receive energy radiated from a source and neural stimulator circuitry configured to deliver electrical stimulus signals to neurons through the at least one electrode for providing stimulation, based at least in part on the received radiated energy.

In another embodiment, the apparatus further comprises a transmitter as a source of the radiated energy; a command receiver configured to receive parameter-setting commands; and a controller coupled with the transmitter and the command receiver, the controller configured to adjust the energy radiated based at least in part on the received parameter-setting commands. The parameter-setting commands may relate to at least one of amplitude, pulse width, or frequency.

In another aspect of the invention, the apparatus further comprises a transmitter coupled with the neural stimulator circuitry; in which the neural stimulator circuitry is further configured to transmit a telemetry signal using the transmitter, the telemetry signal based at least in part on data collected using the at least one electrode for collecting data. The telemetry signal may indicate a strength of stimulus for the energy into the neurons.

The apparatus may further include a second transmitter as a source of the energy radiated; a second receiver configured to wirelessly receive the telemetry signal; and a controller coupled with the transmitter and the second receiver. The controller is preferably configured to (i) compare information of the telemetry signal to a look-up table to estimate a current or a shape; and (ii)) adjust the energy radiated by the second transmitter based at least in part on the estimated current or shape.

In a further aspect of the invention, the controller is configured to, at least one of: amplify, filter, or modulate the received telemetry signal. In still other aspects of the invention, the controller is configured to digitize a modulated telemetry signal with an A-to-D converter.

It is another aspect of the invention to provide an apparatus that comprises one or more dipole or patch antennas coupled with one or more implantable electrode leads.

In another aspect, the present invention further encompasses a first receiver configured to receive the radiated energy via one or more radio frequency (RF) signals.

The present invention further comprises a means for delivering electrical stimulus signals to neurons, comprising at least one electrode for providing stimulation and at least one electrode for collecting data; a means for receiving radiated energy; and a means for converting the received radiated energy into the electrical stimulus signals provided to the at least one electrode for providing stimulation. In still another embodiment, the claimed invention comprises a means for providing the radiated energy; a means for receiving parameter-setting commands; and a means for adjusting the energy radiated based at least in part on the received parameter-setting commands.

Other embodiments of the claimed invention include a means for transmitting a telemetry signal, the telemetry signal based at least in part on data collected using the at least one electrode for collecting data. The telemetry signal may indicate a strength of stimulus provided to the neurons.

In still another embodiment, the claimed invention comprises a means for transmitting the radiated energy; a means for receiving the telemetry signal; and a means for comparing information of the telemetry signal to a look-up table to estimate a current or a shape; and a means for adjusting the energy radiated based at least in part on the estimated current or shape.

Further embodiments include a means for, at least one of: amplifying, filtering, or modulating the received telemetry signal; a means for digitizing the modulated telemetry signal with an A-to-D converter. The system may further comprise one or more dipole or patch antennas coupled with one or more implantable electrode leads.

Additional embodiments include a means for receiving radiated energy in which the radiated energy is received via one or more radio frequency (RF) signals.

Additional embodiments include an implantable lead for wireless neural modulation brain stimulation, the lead comprising at least one electrode for providing stimulation to the neurons to be stimulated; and at least one electrode for collecting data to be provided to device circuitry.

In another aspect of the invention, there is a method of managing a brain impairment condition of a patient. The method includes the steps of: utilizing a wireless receiver for receiving energy radiated from a source; delivering, using the device circuitry, electrical stimulus signals to neurons of a patient diagnosed with a brain disorder through at least one electrode of an electrode lead implanted in the patient, the at least one electrode for providing stimulation, in which the electrical stimulus signals are based at least in part on the received radiated energy; and collecting data, through one or more electrodes of the implanted electrode lead, which are configured to collect data.

The method of managing a brain impairment may further include utilizing a transmitter as a source for transmitting the radiated energy; receiving, by a command receiver, parameter-setting commands; and adjusting, by a controller coupled with the transmitter and the command receiver, the energy radiated, based at least in part on the received parameter-setting commands. Still other embodiments include transmitting, by a transmitter coupled with the device circuitry, a telemetry signal, the telemetry signal based at least in part on data collected using the one or more electrodes.

In still further embodiments, the method includes radiating energy, using a second transmitter; receiving, wirelessly, by a second receiver, a telemetry signal; and comparing, using a controller coupled with the transmitter and the second receiver, information of the telemetry signal to a look-up table to estimate a current or a shape; and adjusting, by the controller, the energy radiated, based at least in part on the estimated current or shape.

A method of the presently claimed invention may also include at least one of amplifying, filtering, or modulating, by the controller, the received telemetry signal. Still other embodiments include a method further comprising: digitizing, by the controller, a modulated telemetry signal with an A-to-D converter.

In certain embodiments, the system can be used for epilepsy. A study on epileptic dogs shows that the wireless deep brain stimulation (DBS) system will allow for recording intracranial signals showing both inter-ictal and ictal activity to localize seizures with and without simultaneous stimulation.

A prototype has been developed and tested in small animal trials (n=6) to assess feasibility in a stereotactic frame of the recording data and stimulating ability to move forward to a full-size human compatible version of the predicate devices, incorporating both recording and stimulating electrodes into one lead. Bench and in vivo testing have shown the feasibility for a final configuration of wireless device. Outcomes include one or more of the following: (i) having the same effectiveness as the predicate stimulation lead in bench trials; (ii) having the same effectiveness as the predicate recording lead; (iii) having the same electrode charge density as the predicate device; (iv) enabling micro-wire integration; and (v) enabling recording analysis in real-time for a device that can be eventually productized to the home market.

Figure 21:
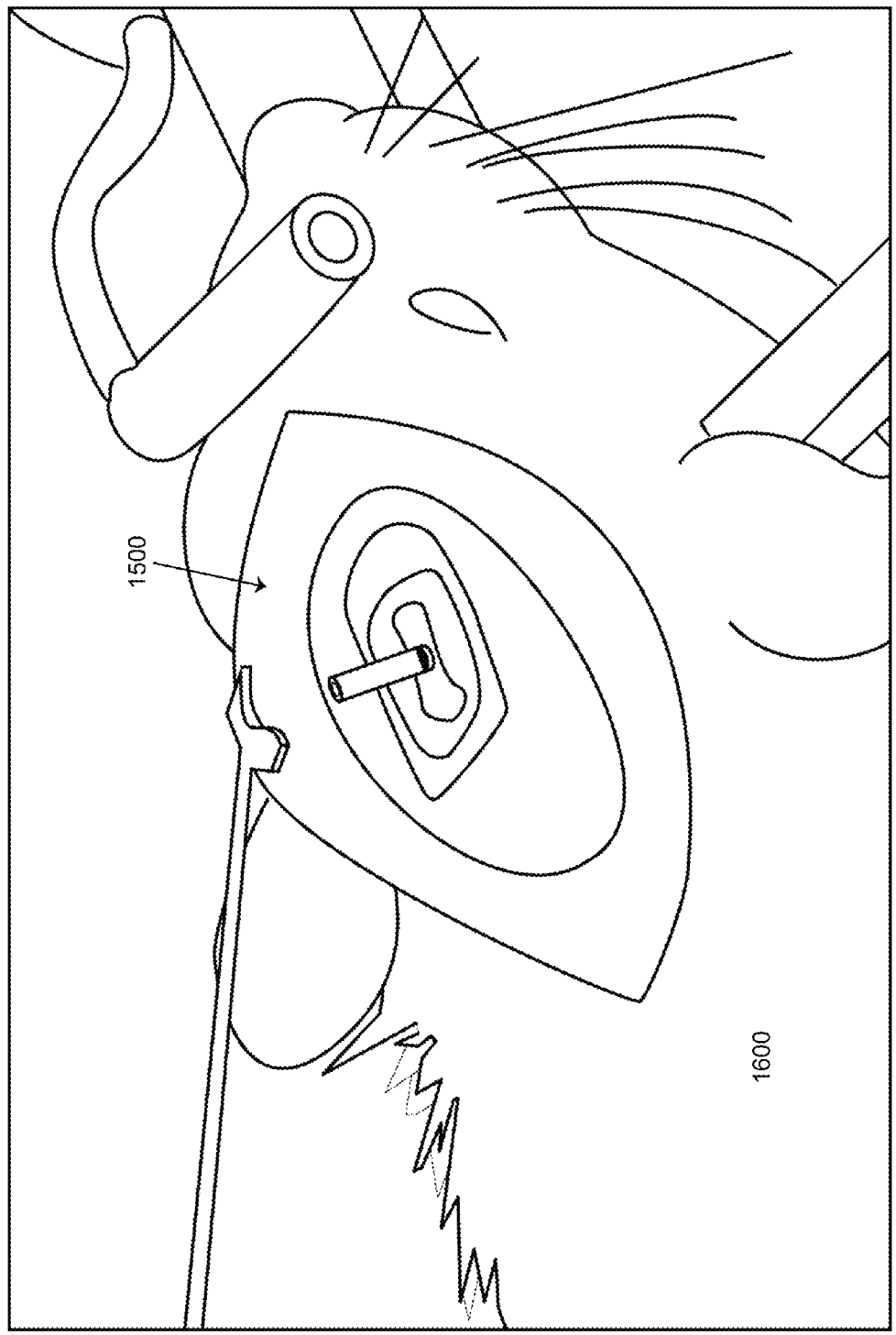
FIG. 21 illustrates the placement of a deep brain stimulator/recording lead 1500 in a rodent model 1600.

FIG. 21 depicts a wireless lead adapted for use in non-human subjects. A deep brain stimulator/recording lead 1500 may be implanted in a rodent model 1600. The deep brain stimulator/recording lead 1500 may be configured for used with the rodent model 1600. For example, the size of the deep brain stimulator/recording lead 1500 may be reduced for use in rodent model 1600.

Figure 22:
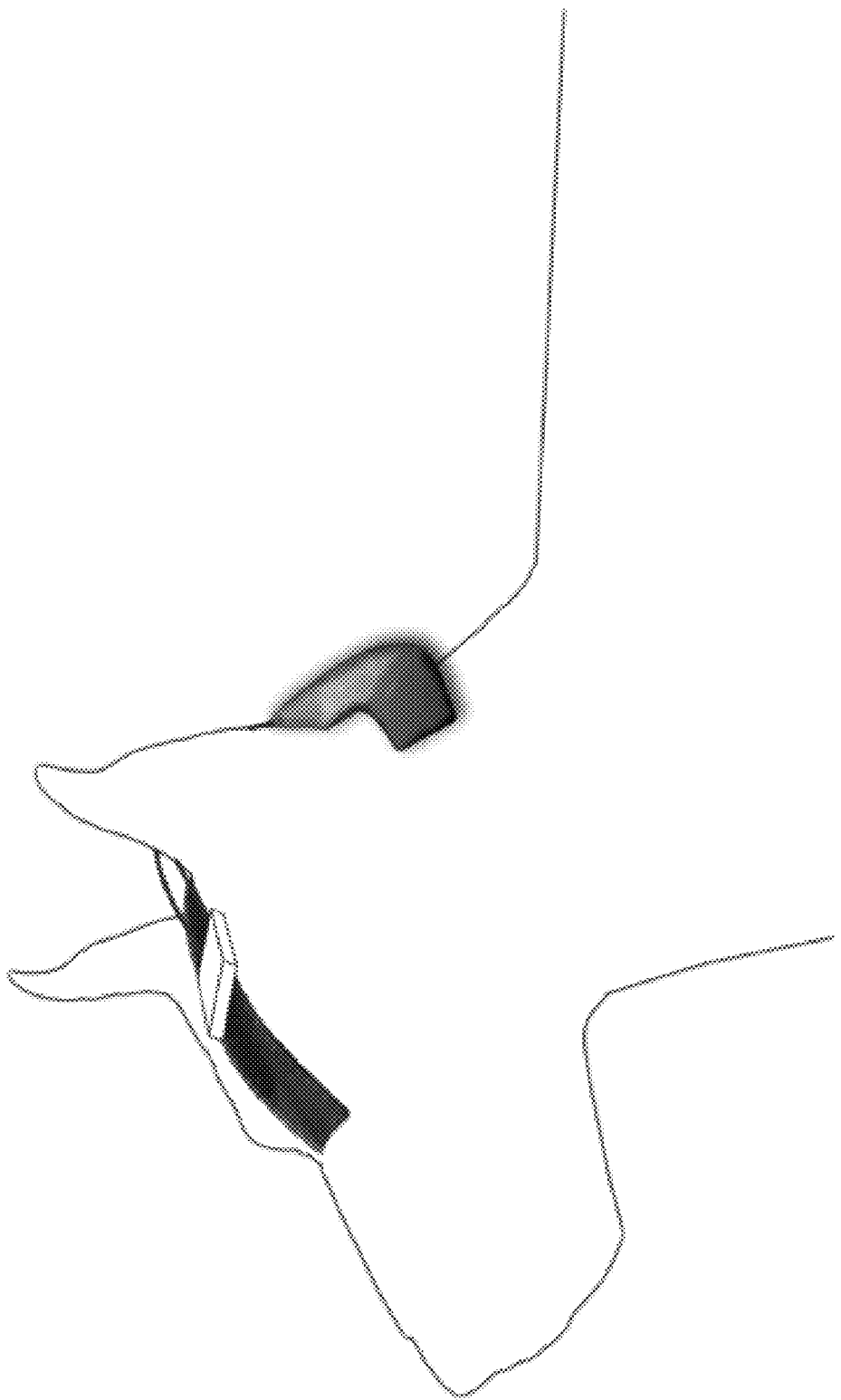
FIG. 22 illustrates the wireless transceiver and pulse generator embodiment on a canine model.

FIG. 22 illustrates the wireless transceiver and pulse generator embodiment on a canine model. The wireless transceiver and pulse generator may be configured for use with a canine model. For example, the wireless transceiver and pulse generator may be shaped so as to secure to the head of a canine model.

Figure 23:
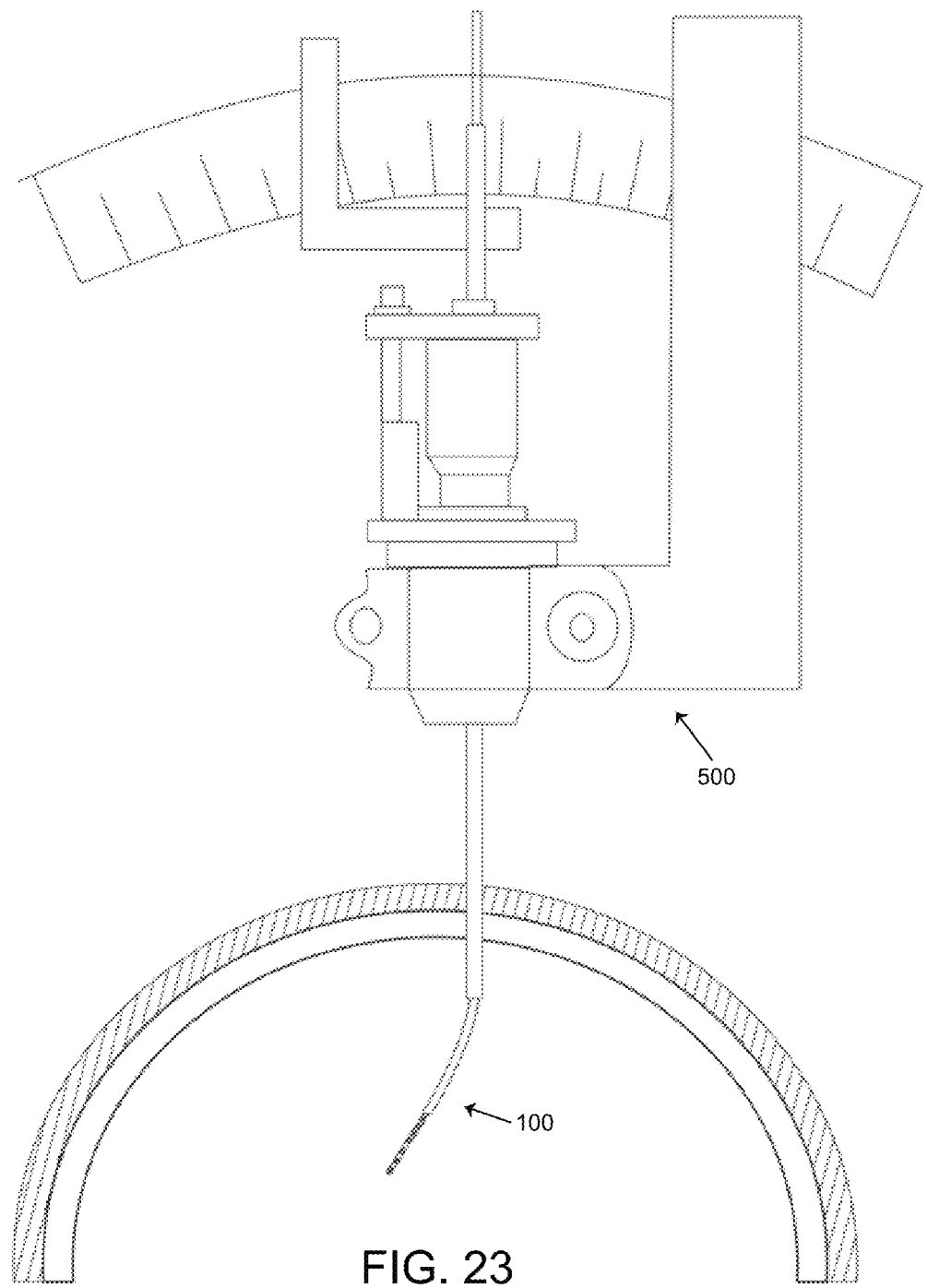
FIG. 23 depicts the stereotactic implantation system 500 used during surgical implantation to ensure that the wireless lead 100 is placed at the anatomical point of therapy.
Figure 24:
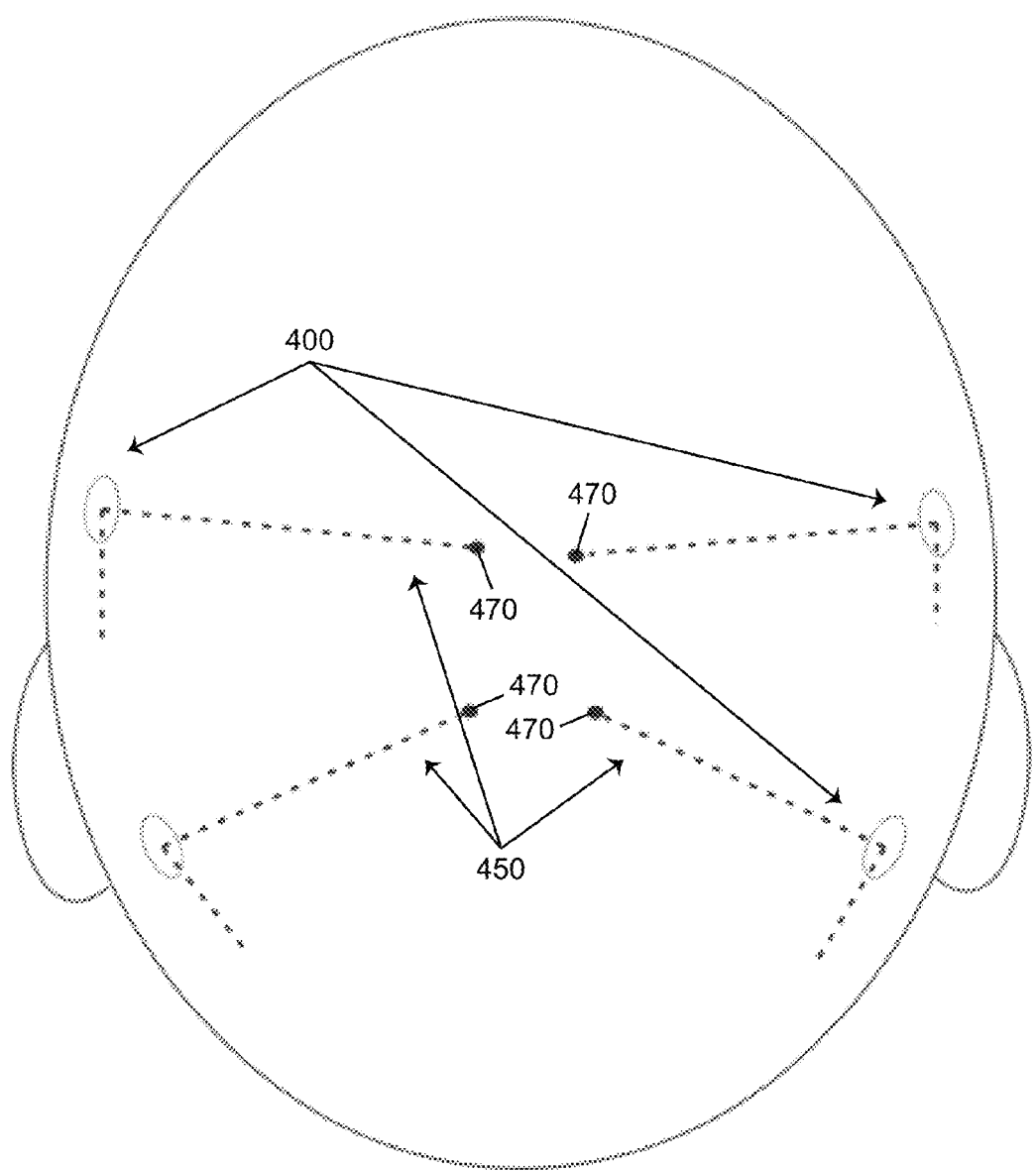
FIG. 24 depicts four anatomical introduction points 400, steering vectors 450, and location for proximal antenna anchor points for implanting wireless deep brain stimulation/recording leads.

FIG. 23 depicts a stereotactic implantation system 500 that may be used during surgical implantation to ensure that the wireless lead 100 is placed at the anatomical point of therapy. In FIG. 24, four anatomical introduction points 400 are depicted. The figure also shows steering vectors 450 and proximal antenna anchor points 470.

Figure 25:
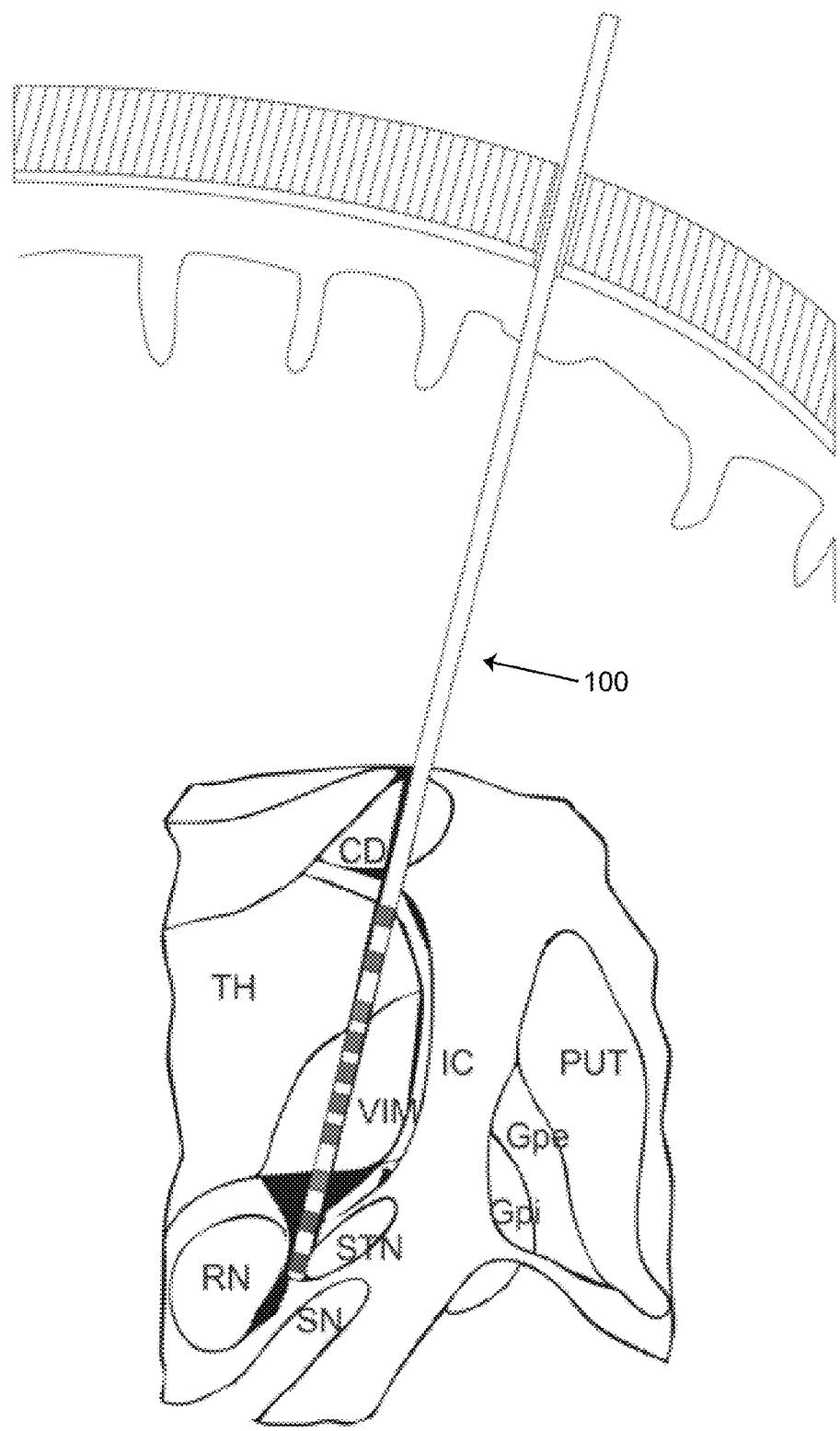
FIG. 25 depicts a wireless deep brain stimulation/recording lead 100 during implantation and the available anatomical termination locations for therapy.
Figure 26:
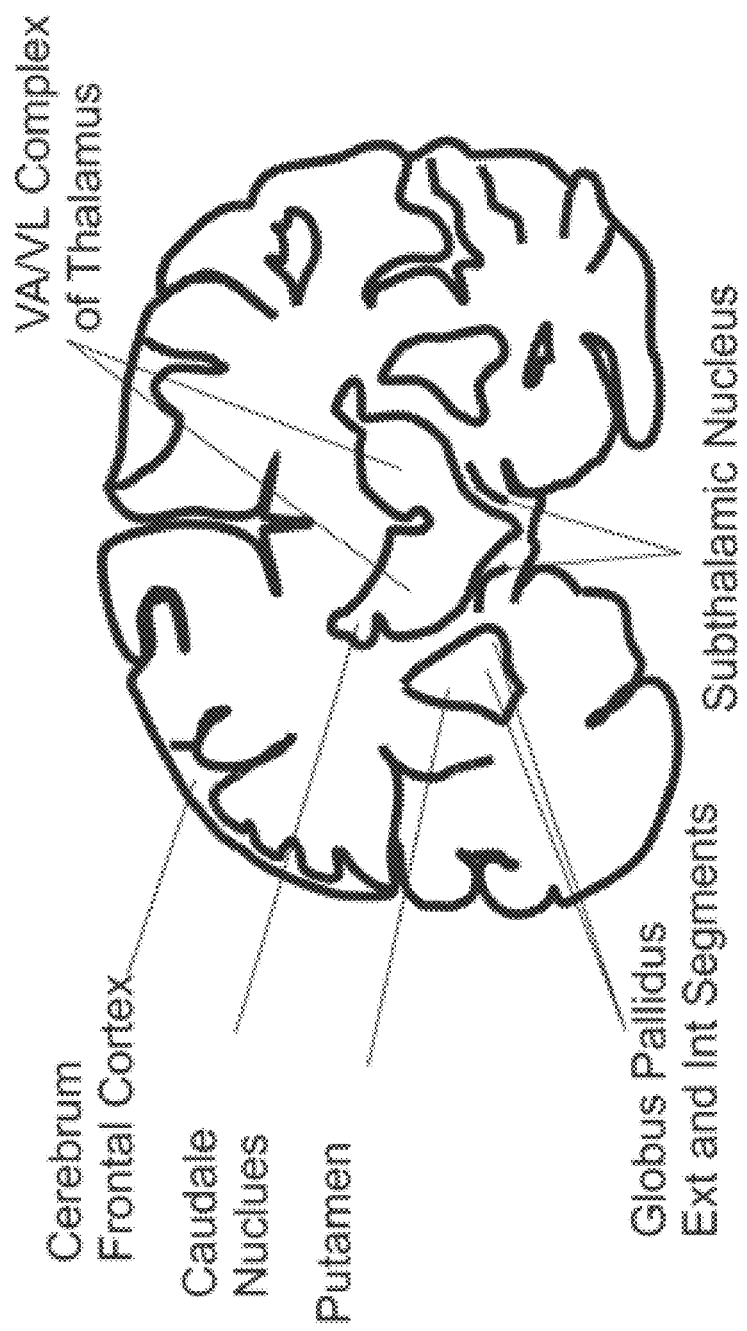
FIG. 26 depicts the human brain and the anatomical locations that are targets for therapy in deep brain stimulation/recording.
Figure 27:
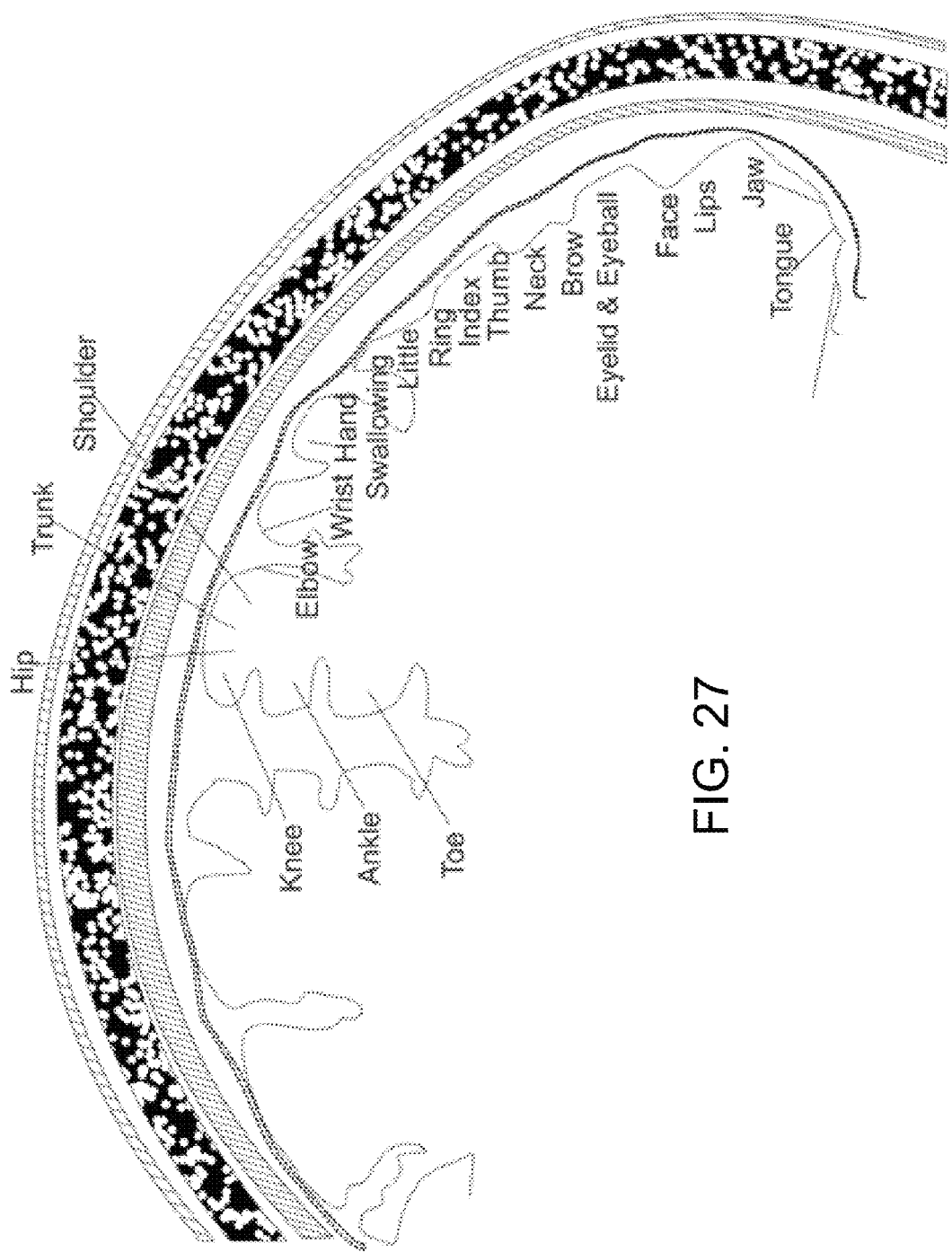
FIG. 27 depicts the human brain and the anatomical locations that are targets for therapy in cortical stimulation/recording.

Anatomical locations for therapy are described in FIGS. 25-27. In the stimulation depiction in FIG. 25, the stimulation/recording lead 100 terminates at an area near the red nucleus (RN) and the subthalamic nucleus (STN). Stimulation and activity observance at the STN is often related to diagnosis and treatment of Parkinson's disease. Deep brain therapy, including recording and stimulation, may also take place in other areas of the brain, such as the areas shown in FIG. 26. For cortical stimulation, FIG. 27 identifies the parts and activities of the body that are controlled at various locations on the cortex, which may be stimulated or recorded according to the exemplary methods disclosed herein.

Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. An apparatus for wireless neural modulation brain stimulation, the apparatus comprising:
   one or more implantable electrode leads configured to be implanted inside a subject's brain to stimulate neurons, each of the one or more electrode leads comprising:
   a lead body that includes a lumen;
   at least one electrode located on the lead body and configured to stimulate the neurons;
   at least one separate electrode located on the lead body and configured to collect data recording neuronal activity inside the subject's brain;
   at least one microwire partially located in the lumen of the lead body and configured to collect data recording single axon neuronal activity inside the patient's brain;
   a first receiver configured to receive energy radiated from a first transmitter that is external to the one or more implantable electrode leads;
   a second transmitter located within the lead body; and
   circuitry configured to use the received energy to:
   deliver electrical stimulus signals to the neurons through the at least one electrode configured to stimulate the neurons; and
   transmit, through the second transmitter, a telemetry signal including(i) the collected data recording neuronal activity inside the subject's brain; and (ii)
   the collected data recording single axon neuronal activity inside the patient's brain.

2. The apparatus of claim 1, further comprising:
   a command receiver configured to receive parameter-setting commands; and
   a controller coupled with the first transmitter and the command receiver, the controller configured to adjust the energy radiated from the first antenna based at least in part on the received parameter setting commands.

3. The apparatus of claim 2, wherein the command receiver is configured to receive the parameter-setting commands that relate to at least one of amplitude, pulse width, or frequency for the electrical stimulus signals.

4. The apparatus of claim 1, in which the telemetry signal indicates a strength of the stimulus signals being delivered to the neurons.

5. The apparatus of claim 1, further comprising:
   a second receiver configured to wirelessly receive the telemetry signal; and a controller coupled with the first transmitter and the second receiver, the controller configured to:
compare information of the telemetry signal to a look-up table to estimate a current or shape of the electrical stimulus signals; and
adjust the energy radiated by the first transmitter based at least in part on the estimated current or shape.

6. The apparatus of claim 5, in which the controller is further configured to perform at least one of: amplify, filter, or modulate the received telemetry signal.

7. The apparatus of claim 6, in which the controller is further configured to digitize a modulated telemetry signal with an A-to-D converter.

8. The apparatus of claim 1, further comprising:
one or more dipole or patch antennas connected to the one or more implantable electrode leads.

9. The apparatus of claim 1, in which the first receiver is configured to receive the radiated energy by receiving one or more radio frequency (RF) signals.

10. The apparatus of claim 1, wherein when the implantable electrode leads are implanted inside the subject's brain, the implantable leads are MRI compatible inside a magnet that is suitable for imaging the subject's brain.

11. The apparatus of claim 1, wherein the electrical stimulus signals are selectively produced and carried to targeted neurons based on the telemetry signal.

12. An implantable lead for wireless neural modulation brain stimulation, the lead comprising:
at least one electrode configured to apply electrical stimulus signals to stimulate neurons of a subject's brain; and
at least one separate electrode configured to collect data recording neuronal activity inside the subject's brain;
at least one microwire configured to collect data recording single axon neuronal activity, wherein, when the implantable lead is implanted inside the subject's brain, the implantable lead is MRI compatible inside a magnet that is suitable for imaging the subject's brain and the implantable lead is wirelessly powered using electrical energy radiated from a separate transmitter.

13. The implantable lead of claim 12, wherein the electrical stimulus signals are selectively produced and carried to targeted neurons based on the collected data recording neuronal activity inside the patient's brain as well as the collected data recording single axon neuronal activity inside the patient's brain.

14. A method of managing a brain impairment condition of a patient, the method comprising:
receiving, using a wireless receiver, energy radiated from a first transmitter that is separate from the wireless receiver;
delivering, using the received energy, electrical stimulus signals to neurons of a patient diagnosed with a brain disorder through at least one electrode of an electrode lead implanted in the patient;
collecting, through one or more electrodes of the implanted electrode lead, data recording neuronal activity inside the patient's brain, the one or more electrodes being separate from the at least one electrode through which electrical stimulus signals are delivered;
collecting, through at least one microwire of the implanted electrode lead, data recording single axon neuronal activity inside the patient's brain; and
transmitting, through a second transmitter within the implanted electrode lead, a telemetry signal including (i) the collected data recording neuronal activity inside the subject's brain; and (ii) the collected data recording single axon neuronal activity inside the patient's brain.

15. The method of claim 14, further comprising:
receiving, by a command receiver, parameter-setting commands; and
adjusting, by a controller coupled with the first transmitter and the command receiver, the energy radiated from the first transmitter, based at least in part on the received parameter-setting commands.

16. The method of claim 15, in which the parameter-setting commands relate to at least one of amplitude, pulse width, or frequency for the electrical stimulus signals.

17. The method of claim 14, in which the telemetry signal indicates a strength of the stimulus signals being delivered to the neurons of the patient.

18. The method of claim 14, further comprising:
receiving, wirelessly, by a second receiver, the telemetry signal; and
comparing, using a controller coupled with the first transmitter and the second receiver, information of the telemetry signal to a look-up table to estimate a current or a shape of the electrical stimulus signals; and
adjusting, by the controller, the energy radiated by the first transmitter, based at least in part on the estimated current or shape.

19. The method of claim 18, further comprising:
amplifying, filtering, or modulating, by the controller, the received telemetry signal.

20. The method of claim 19, further comprising:
digitizing, by the controller, a modulated telemetry signal with an A-to-D converter.

21. The method of claim 14, wherein receiving the radiated energy comprises receiving one or more radio frequency (RF) signals.

22. The method of claim 14, wherein the electrical stimulus signals are selectively produced and carried to targeted neurons based on the telemetry signal.

* * * * *

UNITED STATES PATENT AND TRADEMARK OFFICE
CERTIFICATE OF CORRECTION

PATENT NO. : 9,433,789 B2
APPLICATION NO. : 14/214432
DATED : September 6, 2016
INVENTOR(S) : Laura Tyler Perryman et al.

It is certified that error appears in the above-identified patent and that said Letters Patent is hereby corrected as shown below:

In the Claims

In claim 1, column 12, line 46, delete "including(i)" and insert -- including (i) --, therefor.

Signed and Sealed this
Fifteenth Day of November, 2016

Michelle K. Lee
*Director of the United States Patent and Trademark Office*